United States Patent
Paz et al.

(10) Patent No.: US 12,414,514 B2
(45) Date of Patent: Sep. 16, 2025

(54) TOLERANCE TO ToLCNDV IN CUCUMBER

(71) Applicant: VILMORIN & CIE, Paris (FR)

(72) Inventors: Zahi Paz, Shikmim (IL); Ohad Yogev, Shikmim (IL); Alicia Rodriguez Medina, Aguadulce (ES)

(73) Assignee: VILMORIN & CIE, Paris (FR)

( * ) Notice: Subject to any disclaimer, the term of this patent is extended or adjusted under 35 U.S.C. 154(b) by 738 days.

(21) Appl. No.: 17/628,759

(22) PCT Filed: Jul. 31, 2020

(86) PCT No.: PCT/EP2020/071638
§ 371 (c)(1),
(2) Date: Jan. 20, 2022

(87) PCT Pub. No.: WO2021/019069
PCT Pub. Date: Feb. 4, 2021

(65) Prior Publication Data
US 2022/0279748 A1    Sep. 8, 2022

(30) Foreign Application Priority Data

Jul. 31, 2019   (WO) .................. PCT/IB2019/000916

(51) Int. Cl.
*A01H 6/34*        (2018.01)
*A01H 1/04*        (2006.01)
*A01H 5/08*        (2018.01)

(52) U.S. Cl.
CPC ............. *A01H 6/346* (2018.05); *A01H 1/045* (2021.01); *A01H 5/08* (2013.01)

(58) Field of Classification Search
CPC .................................................. A01H 6/346
See application file for complete search history.

(56) References Cited

FOREIGN PATENT DOCUMENTS

WO    2017/081205 A1    5/2017

OTHER PUBLICATIONS

Saez et al., 2021, Resistant sources and genetic control of resistance to ToLCNDV in cucumber. Microorganisms, 9(5), 913. (Year: 2021).*
Saez et al., 2021, Resistant sources and genetic control of resistance to ToLCNDV in cucumber, Supplementary Table S1. Microorganisms, 9(5), 913. (Year: 2021).*
Indian genotype PI 197087, see Passport Data, collection date of Oct. 6, 1993. (Year: 1993).*
Definition of "bear", Marriam Webster Dictionary, Accessed from https://www.merriam-webster.com/, access date Jan. 7, 2025. (Year: 2025).*
Cucurbit report (Cucurbit Genetics Cooperative Report 33-34: 69-103 (article 23) 2010-2011) (Year: 2011).*
Chang et al., "Identification and characterization of a mechanical transmissible begomovirus causing leaf curl on oriental melon", European Journal of Plant Pathology, (2010), vol. 127, pp. 219-228.
Gao et al., "DNA-guided genome editing using the Natronobacterium gregoryi Argonaute", Nature Biotechnology, (2016), vol. 34, No. 7, pp. 768-773 and retraction.
Huang et al., "The genome of the cucumber, *Cucumis sativus* L.", Nature Genetics, (2009), vol. 41, No. 12, pp. 1275-1281 and online methods.
Islam et al., "Screening of Luffa cylindrica Roem. for resistance against Tomato Leaf Curl New Delhi Virus, Inheritance of resistance, and identification of SRAP markers linked to the single dominant resistance gene", Journal of Horticultural Science and Biotechnology, (2011), vol. 86, No. 6, pp. 661-667.
Ito et al., "Complete nucleotide sequence of a new isolate of tomato leaf curl New Delhi virus infecting cucumber, bottle gourd and muskmelon in Thailand", Arch Virol, (2008), vol. 153, No. 3, pp. 611-613.
Kirkbride J. H. Jr., Biosystematic Monograph of the Genus *Cucumis* (Cucurbitaceae): Botanical Identification of Cucumbers and Melons, (1993).
Li et al., "RNA-Seq improves annotation of protein-coding genes in the cucumber genome", BMC Genomics, (2011), vol. 12:540, pp. 2-11.
Lopez et al., "Mechanical transmission of Tomato leaf curl New Delhi virus to cucurbit germplasm: selection of tolerances sources in Cucumis melo", Euphytica, (2015), vol. 204, pp. 679-691.
Martinez et al., "Screening of Cucurbita germplasm for ToLCNDV resistance under natural greenhouse conditions", ACTA Horticulturae, (2017), No. 1151, pp. 57-62.
Ranjan et al., "Evaluation of cucumber (*Cucumis sativus*) germplasm for agronomic traits and disease resistance and estimation of genetic variability", Indian Journal of Agricultural Sciences, (2015), vol. 85, No. 2, pp. 234-239.

(Continued)

*Primary Examiner* — David H Kruse
*Assistant Examiner* — Santosh Sharma
(74) *Attorney, Agent, or Firm* — Oliff PLC

(57) ABSTRACT

A *Cucumis sativus* var. *sativus* plant tolerant to Tomato Leaf Curl New Delhi Virus (ToLCNDV) includes in its genome the combination of a first quantitative trait locus (QTL) QTL1 on chromosome 1 and a second QTL, QTL2 on chromosome 2, at least one of QTL1 and QTL2 being homozygous, wherein said combination confers to the plant tolerance to ToLCNDV and said QTLs on chromosomes 1 and 2 are present in the genome of the seeds of plant TOCUR6080, NCIMB accession number 43427. The QTL are preferably characterized by defined alleles of different SNPs on chromosomes 1 and 2. Parts of these plants have ToLCNDV tolerance phenotype, as well as progeny, and can be used for introgressing the tolerance in another genetic background, with different methods for obtaining cucumber plants or seeds with increased tolerance to ToLCNDV and different markers linked to the QTLs used to confer tolerance phenotype.

17 Claims, 5 Drawing Sheets
Specification includes a Sequence Listing.

(56) References Cited

OTHER PUBLICATIONS

Ruiz et al., "First Report of Tomato leaf curl New Delhi virus Infecting Tomato in Spain", The American Phytopathological Society, (2015), vol. 99, No. 6, p. 894.
Saeed et al., "A monopartite begomovirus-associated DNA β satellite substitutes for the DNA B of a bipartite begomovirus to permit systemic infection", Journal of General Virology, (2007), vol. 88, pp. 2881-2889.
Saez et al., "Tolerance to ToLCNDV in *Cucurbita* spp.", ACTA Horticulturae, (2017), No. 1151, pp. 31-35.
Tiwari et al., "Molecular detection and identification of Tomato leaf curl New Delhi virus isolate causing yellow mosaic disease in Bitter gourd (*Momordica charantia*), a medicinally important plant in India", Medicinal Plants, (2010), vol. 2(2), pp. 117-123.
Sep. 29, 2020 International Search Report issued in Patent Application No. PCT/EP2020/071638.
Sep. 29, 2022 Written Opinion of the International Searching Authority issued in Patent Application No. PCT/EP2020/071638.

* cited by examiner

TOLERANCE TO ToLCNDV IN CUCUMBER

The present invention relates to resistance and/or tolerance in plants of *Cucumis sativus*, preferably *Cucumis sativus* var. *sativus*, to geminiviruses, especially to begomoviruses, and more specifically to Tomato leaf curl New Delhi virus (ToLCNDV). The present invention also relates to cucumbers, especially cultivated cucumbers, comprising genetic determinants that lead to tolerance and/or resistance to ToLCNDV. The invention further relates to markers linked to the genetic determinants and to the use of such makers to identify or select the genetic determinants and to identify or select plants carrying such tolerance or resistance. The invention also relates to the seeds and progeny of such plants and to propagation material for obtaining such plants, and to different uses of these plants.

BACKGROUND OF THE INVENTION

Cucumber (*Cucumis sativus* L. 2n=2x=14) belongs to the Cucurbitaceae family that includes more than 800 species and is an annual vine plant. Cucumber is one of the most important and widely cultivated vegetables crops, it originates from India, and China is extensively considered as its secondary center of origin. Despite its considerable morphological variability, cucumber showed a narrow genetic base and has a relatively small genome size (350 Mbp), which was sequenced in 2009 (Huang et al. 2009). *Cucumis sativus* houses several botanical varieties including var. *sativus*, the cultivated cucumber and the wild, free-living var. *hardwickii* (R.) Alef. (Kirkbride 1993). A variety of pathogens affect the productivity of cucumber plants including viruses, fungi, bacteria, nematodes, and insects. Cucumbers are inter alia susceptible to many viruses and virus resistance is therefore of major agricultural importance.

The taxonomic family Geminiviridae includes some of the most important plant viruses causing severe diseases in agricultural, ornamental and horticultural crops. Geminiviruses generally are characterized by the unique twin shape of a fused icosahedral viral particle. Geminiviruses are plant viruses which have ambisense single-stranded circular DNA genomes. The genome can either be a single component of 2500-3000 nucleotides, or two similar-sized components. They generally have an elongated, geminate capsid with two incomplete T=I icosahedra joined at the missing vertex. The capsids range from 18-20 nm in diameter with a length of about 30 nm. Viruses with bipartite genomes (begomoviruses only) have these components separated into two different particles, therefore more than one virus particle is required to infect a cell. Transmission of these viruses can be via leafhoppers (mastreviruses, curtoviruses) or via species of whitefly (begomoviruses) or via treehoppers (topocuviruses).

The geminiviruses are responsible for a significant amount of crop damage worldwide. Diseases caused by these viruses have long been recognized as a limitation to the cultivation of several important crops, including maize, cassava, bean, squash, cucurbits, and tomato. Epidemics of geminivirus diseases have arisen due to a number of factors, including the recombination of different geminiviruses co-infecting a plant, which enables novel, possibly virulent viruses to be developed. Other contributing factors include the transport of infected plant material to new locations, expansion of agriculture into new growing areas, and the expansion and migration of vectors that can spread the virus from one plant to another.

Geminiviruses comprise a large and diverse family of viruses that infect a wide range of important monocotyledonous and dicotyledonous crop species and cause significant yield losses. Geminiviruses are classified into four genera: genus Mastrevirus (e.g., Maize streak virus), genus Curtovirus (e.g., Beet curly top virus), genus Begomovirus (e.g., SLCV), and genus Topocuvirus (Tomato pseudo-curly top virus).

The genus Begomovirus contains more than 200 viral species and belong to the taxonomic family Geminiviridae. They are plant viruses that as a group have a very wide host range. Natural hosts of begomoviruses are plant species in which the virus can replicate, cause systemic infection, and encapsidate, and from which virions are ingested and transmitted to a susceptible host by the whitefly vector. Worldwide they are responsible for a large amount of economic damage to many important agronomic and horticultural crops such as tomatoes, beans, squash, cucurbits, cassava and cotton in subtropical and tropical regions of Americas, Africa and Asia. Begomoviruses cause stunting of plants, curling and yellowing of the leaves and low yield of fruits (Saeed et al. 2007). Morphologically, begomovirus particles are non-enveloped. The nucleocapsid is 38 nm long and 15-22 nm in diameter. While particles have basic isocahedral symmetry, they consist of two incomplete icosahedra-missing one vertex-joined together. There are 22 capsomeres per nucleocapsid. Begomovirus species has single stranded closed circular DNA. Most begomoviruses have a bipartite genome, meaning that the genome is segmented into two segments (referred to as DNA A and DNA B) that are packaged into separate particles. Both segments are generally required for successful symptomatic infection in a host cell, but DNA B is dependent for its replication upon DNA A, which can in some begomoviruses apparently cause infections on its own. Tomato leaf curl New Delhi virus (ToLCNDV) is a bipartite begomovirus, with two approximatively 2.7 Kb DNA genomic components designated as DNA-A and DNA-B (circular DNAs) which can cause severe losses in many crops. It was first described on tomatoes in India in 1995, but subsequently, many reports of extensive damages to cucurbit crops have also been made (Chang et al, 2010 and Tiwari et al, 2010), first in other Asian countries and more recently in Europe. Several new disease reports revealed that ToLCNDV caused severe symptoms on bitter gourd, bottle gourd, cantaloupe, cucumber, muskmelon, squash, watermelon and wax gourd, in India, Pakistan, Thailand (Ruiz et al, 2015) and now in Europe and North Africa.

Symptoms include curling and severe mosaic of the young leaves, very short internodes, fruit skin roughness and longitudinal cracking of the fruits, leading to catastrophic losses. It is a whitefly, *Bemisia Tabacci*, transmitted virus (Ruiz et al 2015).

A mechanical inoculation of this virus was developed by Chang et al., 2010 and Lopez et al., 2015. The first description of resistance in Cucurbitaceae plants was on *Luffa cylindrical* by Islam et al., 2011. Plants of *Luffa cylindrical* harboring 2n=24 chromosomes, such a resistance, of monogenic dominant nature, is therefore not likely to be transferable to cucumber background (2n=14). A PCR protocol, specific for ToLCNDV virus detection, was done and described in this same publication. Current methods of preventing and controlling geminiviruses include controlling the spread of insect vectors that carry the virus, developing transgenic plants expressing the viral coat protein, and using classical breeding methods to develop plants having natural resistance to the virus. Development of disease resistant plants offers an effective, safe, and relatively less expensive method of controlling many crop diseases.

Lopez et al 2015 conducted the first published screenings of cucurbit germplasm for the identification of tolerance sources. In general, all sources of *Cucumis sativus* showed severe symptoms and high viral load, identifying them as improper resources for the finding of such resistances.

More interesting results were obtained when looking at *Cucumis metuliferus*, but only one accession was tested, as well as accessions of different genus (namely *Citrullus* and *Cucurbita*). Interesting results were also obtained in *Cucumis melo* subsp. *agrestris* according to this publication.

Ranjan et al, 2015, reports also resistance to ToLCNDV in 13 different indigenous collections of cucumber not suitable for commercial purposes in view of the high number of primary branches; the conditions of ToLCNDV infection and tolerance observations are however not defined in this publication. Moreover, the high percentage of resistant accessions, in contradiction with the results reported in Lopez et al 2015, may indicate that infection quality may have been not sufficient, as experienced by the inventors in the present application (see example 1).

In spite of intensive work in this respect and the importance of cucumber production worldwide, currently, no cultivated *Cucumis sativus* plants reproducibly resistant or tolerant to ToLCNDV have been obtained.

Therefore, there is an important need in the art to identify a reliable source of resistance and/or tolerance which could be used to obtain resistant commercial cultivated plants of *Cucumis sativus* var. *sativus*.

Contrary to the teaching of the prior art, the present inventors have not tried to identify a monogenic resistance in wild or indigenous accessions, but have identified a combination of genetic determinants imparting said resistance or tolerance.

The present invention provides cultivated *C. sativus* plants that display resistance and/or tolerance to Tomato leaf curl New Delhi virus (ToLCNDV), as well as methods that produce or identify cucumber plants that display the resistance and/or tolerance to ToLCNDV, and potentially also to other geminiviruses. The present invention also discloses molecular genetic markers, especially SNPs, linked to the genetic loci conferring resistance and/or tolerance to ToLCNDV.

SUMMARY

The present inventors have identified *C. sativus* plants which display a tolerance and/or resistance to the Tomato leaf curl New Delhi virus and they have been able to localize and identify genetic determinants, also referred hereafter as QTLs (Quantitative Trait Locus) that lead to tolerance and/or resistance to the Tomato leaf curl New Delhi virus, when present in combination.

The tolerance and/or resistance according to the present invention is imparted by the newly discovered genetic determinants, that can confer a satisfying level of tolerance and/or resistance to the Tomato leaf curl New Delhi virus (ToLCNDV) when they are combined. The present invention thus provides these genetic determinants, also here named QTLs.

The present invention provides cultivated cucumber plants that display tolerance and/or resistance to ToLCNDV as well as methods that produce or identify cucumber plants that exhibit tolerance and/or resistance to ToLCNDV. The present invention also discloses molecular genetic markers, especially SNPs, linked to the QTLs that lead to tolerance and/or resistance to the ToLCNDV. Plants obtained through the methods and uses of such molecular markers are also provided.

Said resistance and/or tolerance is moreover easily transferable to different genetic backgrounds and the invention also extends to different methods allowing the transfer or introgression of the QTLs conferring the phenotype.

The invention also provides several methods and uses of the information linked to the SNPs associated to the QTLs conferring ToLCNDV resistance and/or tolerance, inter alia methods for identifying ToLCNDV resistant and/or tolerant plants and methods for identifying further molecular markers linked to this resistance and/or tolerance, as well as methods for improving the yield of cucumber production in an environment infested by ToLCNDV and methods for protecting a cucumber field from ToLCNDV infection or transmission.

Definitions

The term "Resistance" is as defined by the ISF (International Seed Federation) Vegetable and Ornamental Crops Section for describing the reaction of plants to pests or pathogens, and abiotic stresses for the Vegetable Seed Industry. Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

The term "Tolerance" is used herein to indicate a phenotype of a plant wherein at least some of the disease-symptoms remain absent upon exposure of said plant to an infective dose of virus, whereby the presence of a systemic or local infection, virus multiplication, at least the presence of viral genomic sequences in cells of said plant and/or genomic integration thereof can be established, at least under some culture conditions. Tolerant plants are therefore resistant for symptom expression but symptomless carriers of the virus. Sometimes, viral sequences may be present or even multiply in plants without causing disease symptoms. It is to be understood that a tolerant plant, although it is infected by the virus, is generally able to restrict at least moderately the growth and development of the virus. Moreover, some plants may be tolerant under some culture conditions, and resistant under different conditions. Tolerance and Resistance are thus not mutually exclusive.

Symptoms on leaves of ToLCNDV infection generally include yellowy green mosaic symptoms.

Susceptibility: The inability of a plant variety to restrict the growth and development of a specified pest or pathogen; a susceptible plant displays the detrimental symptoms linked to the virus infection, namely the foliar damages and fruit damages in case of ToLCNDV infection.

A *Cucumis sativus* plant susceptible to ToLCNDV, is for example the commercially available variety Trimax F1, or Misil F1, or Falconstar F1. All commercially available varieties of cucumbers are, to date, susceptible to ToLCNDV, before the present invention.

A plant according to the invention has thus at least improved tolerance or resistance to ToLCNDV, with respect to the variety Trimax F1, and more generally with respect to any commercial variety of cucumber. The resistance of the invention is a resistance to the ToLCNV, especially to the severe strains, giving rise to the more severe symptoms.

As used herein, the term "offspring" or "progeny" refers to any plant resulting as progeny from a vegetative or sexual reproduction from one or more parent plants or descendants thereof. For instance, an offspring plant may be obtained by cloning or selfing of a parent plant or by crossing two parental plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "genetic determinant" and/or "QTL" refers to any segment of DNA associated with a biological function. Thus, QTLs and/or genetic determinants include, but are not limited to, genes, coding sequences and/or the regulatory sequences required for their expression. QTLs and/or genetic determinants can also include nonexpressed DNA segments that, for example, form recognition sequences for other proteins.

As used herein, the term "genotype" refers to the genetic makeup of an individual cell, cell culture, tissue, organism (e.g., a plant), or group of organisms.

As used herein, the term "grafting" is the operation by which a rootstock is grafted with a scion. The primary motive for grafting is to avoid damages by soil-born pest and pathogens when genetic or chemical approaches for disease management are not available. Grafting a susceptible scion onto a resistant rootstock can provide a resistant cultivar without the need to breed the resistance into the cultivar. In addition, grafting may enhance tolerance to abiotic stress, increase yield and result in more efficient water and nutrient uses.

As used herein, the term "heterozygote" refers to a diploid or polyploid individual cell or plant having different alleles (forms of a given gene, genetic determinant or sequences) present at least at one locus.

As used herein, the term "heterozygous" refers to the presence of different alleles (forms of a given gene, genetic determinant or sequences) at a particular locus.

As used herein, "homologous chromosomes", or "homologs" (or homologues), refer to a set of one maternal and one paternal chromosomes that pair up with each other during meiosis. These copies have the same genes in the same loci and the same centromere location.

As used herein, the term "homozygote" refers to an individual cell or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "locus" (plural: "loci") refers to any site that has been defined genetically, this can be a single position (nucleotide) or a chromosomal region. A locus may be a gene, a genetic determinant, or part of a gene, or a DNA sequence, and may be occupied by different sequences. A locus may also be defined by a SNP (Single Nucleotide Polymorphism), by several SNPs, or by two flanking SNPs.

As used herein, the term "rootstock" is the lower part of a plant capable of receiving a scion in a grafting process.

As used herein, the term "scion" is the higher part of a plant capable of being grafted onto a rootstock in a grafting process.

The invention encompasses plants of different ploidy levels, whether a diploid plant, but also a triploid plant, a tetraploid plant, etc.

In the context of the present invention, DNA strand and allele designation and orientation for the SNP markers is done according to the TOP/BOT method developed by Illumina (illumina.com/documents/products/technotes/technote_topbot.pdf).

DETAILED DESCRIPTION OF THE INVENTION

The present inventors have identified two QTLs which, when present in a *C. sativus* plant, in combination, provide an improved tolerance and/or resistance to these plants when infected or likely to be infected by the Tomato leaf curl New Delhi virus (ToLCNDV).

These two QTLs, namely QTL1 and QTL2, when simultaneously present in a *C. sativus* background, especially on chromosomes 1 and 2 respectively, confer an improved tolerance and/or resistance to ToLCNDV.

The phenotype of the plants according to the invention is, in most circumstances, best characterized as tolerance rather than resistance to ToLCNDV; under specific circumstances, the plants of the invention however exhibit resistance to ToLCNDV. In the following, reference is made to tolerance to ToLCNDV; this phenotype however encompasses resistance phenotype, under specific circumstances. Plants of the invention may also behave as symptomless carriers, under certain conditions. Therefore, in the following any reference to tolerance or tolerance phenotype can be substituted by a reference to resistance, or by a reference to resistance and/or tolerance.

The present invention is directed to *Cucumis sativus* plants, preferably *Cucumis sativus* var. *sativus* plants that exhibit tolerance to geminiviruses, and more specifically tolerance to ToLCNDV, as well as methods that produce or identify *C. sativus* var. *sativus* plants that exhibit tolerance to ToLCNDV infection. The present invention also discloses molecular genetic markers, especially SNPs, linked to the tolerance loci.

The tolerance according to the invention is preferably in response to any type of infection, either natural infection or mechanical inoculation, and in any event it is at least tolerance to natural infection by ToLCNDV, especially natural infection transmitted by *Bemisia tabacci*. As stressed above, any reference to tolerance can be substituted by a reference to resistance, or to resistance and/or tolerance.

The tolerance according to the invention is preferably characterized by the absence of all the symptoms generally associated with ToLCNDV infection, especially severe ToLCNDV, namely leaves in upper part of plant showing yellowing mosaic, puckering and stunting of the plant, upon exposure to the virus, in natural infection conditions.

According to a first aspect, the present invention is thus directed to a *C. sativus* var. *sativus* plant or seed, which is tolerant to ToLCNDV, comprising in its genome two QTLs, namely QTL1 and QTL2, which confer said tolerance to ToLCNDV when present in combination. QTL1 is preferably localized on chromosome 1 and QTL2 is on chromosome 2. The invention is also directed to a cell of such a plant or seed, comprising these QTLs sequences.

Whereas each QTL, taken in isolation, may provide a minor level of tolerance to ToLCNDV, such a level is insufficient to reproducibly diminish the loss in productivity of the plant, in case of ToLCNDV infection, irrespectively of the strain of ToLCNDV. The combination of both QTLs is thus necessary to confer a reliable level of ToLCNDV tolerance, irrespective of the infecting strain of ToLCNDV. The level of ToLCNDV tolerance imparted by said QTLs is however increased if at least one of the two QTLs is present homozygously. The invention is thus more specifically directed to plants comprising in their genome QTL1 on chromosome 1 and QTL2 on chromosome 2, which confer in combination tolerance to ToLCNDV, wherein at least one of those two QTLs is present homozygously in the genome of said plant, seed or cell, thus imparting a sufficient tolerance level. According to an even more preferred embodiment, both QTLs are homozygously present.

The plant according to the invention is preferably a cultivated cucumber, namely a cultivated *C. sativus* var. *sativus* plant.

The QTLs according to the invention and conferring the improved tolerance to ToLCNDV are preferably chosen from the ones present in the genome of seeds of TOCUR6080. A sample of this *C. sativus* var. *sativus* seed has been deposited by Hazera Seeds Ltd. Berurim, M. P. Shikmim 79837, Israel, pursuant to and in satisfaction of the requirements of the Budapest treaty on the International Recognition of the deposit of Microorganisms for the Purpose of Patent procedure ("the Budapest Treaty" with the National collection of Industrial, Food and Marine bacteria (NCIMB) (NCIMB, Ltd, Ferguson Building, Craibstone Estate, Bucksburn, Aberdeen AB21 9YA, united Kingdom) on Jun. 24, 2019 under accession number NCIMB 43427. A deposit of this cucumber seed is maintained by Hazera Seeds Ltd. Berurim, M. P. Shikmim 79837, Israel.

The plants grown from these deposited seeds are plants tolerant or resistant to ToLCNDV, and have moreover elongated fruits, with a green skin and not a bitter test.

The QTLs conferring the improved tolerance to ToLCNDV are preferably located on chromosome 1 for QTL1 and on chromosome 2 for QTL2. They are more preferably located within a chromosomal interval of chromosome 1 which comprises or is delimited by the SNP CU-0002005 (SEQ ID NO:1) and the SNP CU-0001983 (SEQ ID NO:12) for QTL1, and within a chromosomal interval of chromosome 2 which comprises or is delimited by the SNP CU-0000463 (SEQ ID NO:13) and the SNP CU-0006479 (SEQ ID NO:27) for QTL2.

The specific polymorphisms corresponding to the SNPs (Single Nucleotide Polymorphism) referred to in this description, as well as the flanking sequences of these SNPs in the *C. sativus* genome, are given in the experimental section (see inter alia tables 3 and 4 for chromosomes 1 and 2 respectively, and example 3 for chromosome 4) and the accompanying sequence listing. Their location in the cucumber genome "genome v2.0, Chinese Long IL 9930", available at cucurbitgenomics.org/organism/2 (based on Huang et al, 2009 and Li et al, 2011), on chromosomes 1, 2 and 4, is indicated respectively in tables 3 and 4, and in example 3, as well as their flanking sequences, and in the sequence listing.

It is to be noted in this respect that, by definition, a SNP refers to a single nucleotide in the genome, which is variable depending on the allele which is present, whereas the flanking nucleotides are identical. For ease of clear identification of the position of the different SNPs, their position is given in tables 3 and 4 by reference to the cucumber genome sequence and by reference to their flanking sequences, identified by SEQ ID number. In the sequence associated with a specific SNP in the present application, for example SEQ ID NO:1 for the SNP CU-0002005, only one nucleotide within the sequence actually corresponds to the polymorphism, namely the $36^{th}$ nucleotide of SEQ ID NO:1 corresponds to the polymorphic position of SNP CU-0002005, which can be A or G as indicated in table 3. The flanking sequences are given for positioning the SNP in the genome but are not part of the polymorphism as such.

The present inventors have identified that the QTLs responsible for the phenotype of interest, i.e. an improved tolerance to ToLCNDV are to be found in the chromosomal regions mentioned above, by identifying the presence of sequences at different loci along said region, namely at 27 different loci defined by the 27 following SNPs: CU-0002005 (SEQ ID NO:1), CU-0000824 (SEQ ID NO:2), CU-0001679 (SEQ ID NO:3), CU-0000195 (SEQ ID NO:4), CU-0000697 (SEQ ID NO:5), CU-0000649 (SEQ ID NO:6), CU-0002031 (SEQ ID NO:7), CU-0000366 (SEQ ID NO:8), CU-0000554 (SEQ ID NO:9), CU-0000744 (SEQ ID NO:10), CU-0006168 (SEQ ID NO:11) and CU-0001983 (SEQ ID NO:12) for QTL1 on chromosome 1 and CU-0000463 (SEQ ID NO:13), CU-0001997 (SEQ ID NO:14), CU-0001204 (SEQ ID NO:15), CU-0003652 (SEQ ID NO:16), CU-0002682 (SEQ ID NO: 17), CU-0005012 (SEQ ID NO:18), CU-0001371 (SEQ ID NO:19), CU-0002276 (SEQ ID NO: 20), CU-0001479 (SEQ ID NO:21), CU-0006476 (SEQ ID NO:22), CU-0003181 (SEQ ID NO: 23), CU-0001663 (SEQ ID NO:24), CU-0001531 (SEQ ID NO:25), CU-0001495 (SEQ ID NO: 26) and CU-0006479 (SEQ ID NO:27) for QTL2 on chromosome 2.

A cucumber plant according to the invention having an improved tolerance to ToLCNDV has QTL imparting said phenotype at at least one of the loci on chromosome 1 and at at least one of the loci on chromosome 2. Preferred SNPs on chromosome 1 are CU-0000649, CU-0002031, CU-0000366, CU-0000554 and CU-0000744 for QTL1 and CU-0003652, CU-0002682, CU-0005012 and CU-0001371 for chromosome 2.

Therefore, according to another embodiment of the invention, the QTLs present in the genome of a plant, seed or cell of the invention are preferably to be found at least at two or more of the 27 loci encompassing said 27 SNPs mentioned above, namely at one or more of the loci encompassing CU-0002005, CU-0000824, CU-0001679, CU-0000195, CU-0000697, CU-0000649, CU-0002031, CU-0000366, CU-0000554, CU-0000744, CU-0006168 and CU-0001983 on chromosome 1, and at one or more of the loci encompassing CU-0000463, CU-0001997, CU-0001204, CU-0003652, CU-0002682, CU-0005012, CU-0001371, CU-0002276, CU-0001479, CU-0006476, CU-0003181, CU-0001663, CU-0001531, CU-0001495 and CU-0006479 on chromosome 2.

The alleles of the 27 SNPs of the invention corresponding to the QTLs conferring the ToLCNDV tolerance are allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168 and allele G of CU-0001983 for QTL1 on chromosome 1 and allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479 for QTL2 on chromosome 2. There are reported in tables 3, 4 and 5 of the experimental section. The presence of the QTLs conferring the tolerance to ToLCNDV can be revealed by the presence of said specific alleles. The alleles of these SNPs can thus reflect the presence of the QTLs of the invention. At least two SNPs, one on chromosome 1 and one on chromosome 2 are to be checked for reflecting the presence of the QTLs on chromosomes 1 and 2.

According to a preferred embodiment of the present invention, the QTLs conferring the tolerance to ToLCNDV are on one or more chromosomal intervals delimited by the SNPs of the present invention.

According to this embodiment, the QTL1 is on a chromosomal interval of chromosome 1 delimited on one side by SNP CU-0002005 and on the other side by SNP CU-0001983, preferably on the interval between SNP CU-0002005 (SEQ ID NO:1) and CU-0006168 (SEQ ID NO:11), more preferably on an interval delimited on one side by CU-0000649 and on the other side by CU-0000554, and even more preferably on an interval delimited on one side by CU-0002031 and on the other side by CU-0000366.

According to another embodiment, the QTL2 is on a chromosomal interval of chromosome 2 delimited on one side by SNP CU-0000463 and on the other side by SNP CU-0006479, preferably on the interval between SNP CU-0000463 (SEQ ID NO:13) and CU-0002276 (SEQ ID NO:20), more preferably on an interval delimited on one side by CU-0003652 and on the other side by CU-0001371, and even more preferably on an interval delimited on one side by CU-0002682 and on the other side by CU-0005012.

It is noted in this respect that specific positions in a chromosome can indeed be defined with respect to single nucleotide polymorphism, insofar as the flanking sequences of said SNPs are defined in order to unambiguously position them on the genome. The present inventors have used SNPs, identified by their flanking sequences, with different alleles, to identify and follow the QTLs of the present invention.

A chromosomal region delimited by two SNPs X and Y refers to the section of the chromosome lying between the positions of these two SNPs and comprising said SNPs, therefore the nucleotide sequence of this chromosomal region begins with the nucleotide corresponding to SNP X and ends with the nucleotide corresponding to SNP Y, i.e. the SNPs are comprised within the region they delimit, according to the invention.

In a plant, seed or cell of the invention, the presence of the QTLs conferring the phenotype of interest is preferably characterized by CU-0002005, CU-0000824, CU-0001679, CU-0000195, CU-0000697, CU-0000649, CU-0002031, CU-0000366, CU-0000554, CU-0000744, CU-0006168 and/or CU-0001983 for the QTL1 on chromosome 1 and by CU-0000463, CU-0001997, CU-0001204, CU-0003652, CU-0002682, CU-0005012, CU-0001371, CU-0002276, CU-0001479, CU-0006476, CU-0003181, CU-0001663, CU-0001531, CU-0001495 and/or CU-0006479 for the QTL2 on chromosome 2.

When present in combination in the genome of a cucumber plant according to the invention, QTL1 and QTL2 will confer collectively tolerance to ToLCNDV. Preferably, in order to provide a suitable or sufficient level of tolerance, at least one of those two QTLs is present homozygously. According to another embodiment, both QTLs are present homozygously.

The invention is also directed to hybrid plants of *C. sativus*, obtainable by crossing a plant having the improved phenotype and bearing homozygously the two QTLs of the invention, with another *C. sativus*. If the other *C. sativus* crossing partner is devoid of the QTLs of the present invention, the hybrid resulting from the cross will harbor the QTLs of the present invention in a heterozygous state and the cucumber plants will also have the tolerance phenotype, although the level of ToLCNDV tolerance will be intermediate.

Preferably, a *C. sativus* plant according to the invention is a cultivated plant or line, more preferably a commercial plant or line. Such a plant or line thus has generally 4 primary branches or less, generally less than 3, for example 2 primary branches, and more preferably has a single primary branch.

Such a commercial plant or line preferably also exhibits resistance to other viruses, especially to potyviruses. Preferably a commercial plant is resistant to ZYMV and/or to CVYV and/or to CYSDV. Resistances to PRSV and CMV are also generally found in commercial plants. Another resistance is powdery mildew (caused by *Podospharea xanthii*) resistance. A plant of the invention is thus advantageously resistant at least to powdery mildew and to potyviruses.

Other resistances or tolerances are also envisaged according to the invention, inter alia resistance to downy mildew caused *Pseudoperonospora cubensis*, resistance to Fusaria caused by *Fusarium oxysporum* f.sp. cucumerinum or by *Fusarium oxysporum* f.sp. *radicis cucumerinum*, resistance to Scab caused by *Cladosporium* cucumerinum, resistance to CGMMV, to WMV, to CYSDV and to CCYV.

Advantageously, a plant of the invention is also resistant to one or more arthropod pests, such as Western flower Thrips (*Franklineilla occidentalis*), Silver leaf white fly (*Bemisia tabaci*), Glasshouse whitefly (*Trialeurodes vaporariorum*) and Root-knot nematode (*Meloidogyne incognita*).

According to still another embodiment, a plant of the invention is used as a scion or as a rootstock in a grafting process. Grafting is a process that has been used for many years in crops such as cucurbitacea. Grafting may be used to provide a certain level of resistance to telluric pathogens such as *Phytophthora* or to certain nematodes. Grating is therefore intended to prevent contact between the plant or variety to be cultivated and the infested soil. The variety of interest used as the graft or scion, optionally an F1 hybrid, is grafted onto the tolerant plant used as the rootstock. The tolerant rootstock remains healthy and provides, from the soils, the normal supply for the graft that it isolates from the diseases.

A plant according to the invention is preferably a gynoecious plant, or a monoecious plant, with at least 50% of gynoecious flowers, even more preferably at least 70 or 80% gynoecious flowers. Moreover, a commercial plant of the invention gives rise to fruits in suitable conditions, 50% of which are at least more than 10 cm long at full maturity, preferably more than 15 or 20 cm at full maturity. The harvested fruits have a green skin color, they preferably have an elongated form.

As detailed above, the invention is directed to *C. sativus* plants, exhibiting the ToLCNDV tolerance, as well as to seeds giving rise to those plants, and cells of these plants or seeds, comprising the tolerance QTLs.

The invention encompasses plants, seeds and cells of any ploidy levels, it encompasses inter alia diploid, triploid, tetraploid and/or allopolyploid plants, cells or seeds.

A plant or seed according to the invention may be a progeny or offspring of a plant grown from the deposited seeds TOCUR6080, deposited at the NCIMB under the accession number NCIMB 43427. Plants grown from the deposited seeds are indeed homozygous for the QTLs of the invention conferring the improved phenotype, they thus bear in their genome the QTLs of interest on each of the homologues of chromosomes 1 and 2. They can be used to transfer these sequences into another background by crossing and selfing and/or backcrossing.

The invention is also directed to the deposited seeds of TOCUR6080 (NCIMB 43427) and to plants grown from one of these seeds. These seeds contain homozygously the QTLs conferring the phenotype of interest. It is noted that these seeds do not correspond to a plant variety, they are not homozygous for most of the genes except the QTLs of the invention; their phenotype is thus not fixed during propagation, except for the tolerance of the invention; most of their phenotypic traits segregate during propagation, with the exception of ToLCNDV tolerance of the invention.

The invention is also directed to plants or seeds as defined above, i.e. containing the two QTLs of interest in homozygous or heterozygous state, but most preferably at least one of those two in homozygous state, said QTLs conferring the ToLCNDV tolerance, wherein these plants or seeds are obtainable by transferring the QTLs from a C. sativus plant, representative seeds thereof were deposited under NCIMB accession NCIMB 43427, into another C. sativus genetic background, for example by crossing said deposited plant with a second cucumber plant parent and selection of the plant bearing the QTLs responsible for the phenotype of interest. During such crossing, QTL1 and QTL2 can be transferred.

It is noted that the seeds or plants of the invention may be obtained by different processes, and are not exclusively obtained by means of an essentially biological process.

According to such an aspect, the invention relates to a cultivated cucumber plant or seed, preferably a non-naturally occurring cucumber plant or seed, which may comprise one or more mutations in its genome, which provides the plant with tolerance to Tomato leaf curl New Delhi virus, which mutation is as present, for example, in the genome of plants of which a representative sample was deposited with the NCIMB under deposit number NCIMB 43427.

In another embodiment, the invention relates to a method for obtaining a cucumber plant or seed carrying one or more mutations in its genome, which provides the plant with tolerance to ToLCNDV. Such a method is illustrated in example 6 and may comprise:
 a) treating M0 seeds of a cucumber plant to be modified with a mutagenic agent to obtain M1 seeds;
 b) growing plants from the thus obtained M1 seeds to obtain M1 plants;
 c) producing M2 seeds by self-fertilization of M1 plants; and
 d) optionally repeating step b) and c) n times to obtain M1+n seeds.

The M1+n seeds are grown into plants and submitted to ToLCNDV infection. The surviving plants, or those with the milder symptoms of ToLCNDV infection, are multiplied one or more further generations while continuing to be selected for their tolerance to ToLCNDV.

In this method, the M1 seeds of step a) can be obtained via chemical mutagenesis such as EMS mutagenesis. Other chemical mutagenic agents include but are not limited to, diethyl sufate (des), ethyleneimine (ei), propane sultone, N-methyl-N-nitrosourethane (mnu), N-nitroso-N-methyl-urea (NMU), N-ethyl-N-nitrosourea (enu), and sodium azide.

Alternatively, the mutations are induced by means of irradiation, which is for example selected from x-rays, fast neutrons, UV radiation.

In another embodiment of the invention, the mutations are induced by means of genetic engineering. Such mutations also include the integration of sequences conferring the ToLCNDV tolerance, as well as the substitution of residing sequences by alternative sequences conferring the ToLCNDV tolerance. Preferably, the mutations are the integration of the two QTLs, QTL1 and QTL2 as described above, in replacement of the homologous sequences of a C. sativus plant. Even more preferably, the mutations are the substitutions of the sequences comprised within SNP CU-0002005 and SNP CU-0001983 on chromosome 1 and within SNP CU-0000463 and CU-0006479 on chromosome 2 of the C. sativus genome, or fragments thereof, by the homologous sequences on chromosomes 1 and 2 respectively, present in the genome of a plant of which a representative sample was deposited with the NCIMB under deposit number NCIMB 43427, wherein the sequences or fragments thereof confer tolerance to ToLCNDV when present simultaneously.

The genetic engineering means which can be used include the use of all such techniques called New Breeding Techniques which are various new technologies developed and/or used to create new characteristics in plants through genetic variation, the aim being targeted mutagenesis, targeted introduction of new genes or gene silencing (RdDM). Example of such new breeding techniques are targeted sequence changes facilitated through the use of Zinc finger nuclease (ZFN) technology (ZFN-1, ZFN-2 and ZFN-3, see U.S. Pat. No. 9,145,565), Oligonucleotide directed mutagenesis (ODM), Cisgenesis and intragenesis, Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535), the CRISPR/Cas system (see U.S. Pat. Nos. 8,697,359; 8,771,945; 8,795,965; 8,865, 406; 8,871,445; 8,889,356; 8,895,308; 8,906,616; 8,932, 814; 8,945,839; 8,993,233; and 8,999,641), engineered meganuclease re-engineered homing endonucleases, DNA guided genome editing (Gao et al., Nature Biotechnology (2016)), and Synthetic genomics. A major part of targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques-State-of-the-art and prospects for commercial development".

The invention in another aspect also concerns any plant likely to be obtained from seed or plants of the invention as described above, and also plant parts of such a plant, and most preferably explant, scion, cutting, seed, fruit, root, rootstock, pollen, ovule, embryo, protoplast, leaf, anther, stem, petiole, and any other plants part, wherein said plant, explant, scion, cutting, seed, fruit, root, rootstock, pollen, ovule, embryo, protoplast, leaf, anther, stem, petiole, and/or plant part is obtainable from a seed or plant according to the first aspect of the invention, i.e. bearing the two QTLs of interest, in combination, homozygously or heterozygously in their genome, wherein preferably at least one of those two QTLs is present homozygously. These plant parts, inter alia explant, scion, cutting, seed, fruit, root, rootstock, pollen, ovule, embryo, protoplast, leaf, anther, stem or petiole, comprise in their genome the QTLs conferring the phenotype of interest when present in combination, i.e. tolerance to ToLCNDV; they thus comprise a cell comprising these QTLs.

According to a preferred embodiment, the invention is directed to seed as described above, which develops into a plant according to the first aspect of the invention, thus tolerant to ToLCNDV infection.

The QTLs referred to in this aspect of the invention are those defined above in the context of plants of the invention. The different features of the QTLs defined in relation with the first aspect of the invention apply mutatis mutandis to this aspect of the invention. The QTLs are thus preferably chosen from those present in the genome of a plant corresponding to the deposited material TOCUR6080 (NCIMB accession number 43427). They are advantageously characterized by the presence of allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168, allele G of CU-0001983, allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479, depending on the QTL of interest. Preferably, amongst the two tolerance QTLs which are present in combination, at least one is present homozygously, and thus also the corresponding alleles.

The invention is also directed to cells of *C. sativus* plants, such that these cells comprise, in their genome, the QTLs of the present invention conferring ToLCNDV tolerance to a *C. sativus* plant, when they are present in combination. The QTLs are those already defined in the context of the present invention, they are characterized by the same features and preferred embodiments already disclosed with respect to the plants and seeds according to the preceding aspects of the invention. The presence of these QTLs can be revealed by the techniques disclosed above and well known to the skilled reader. It can inter alia be determined whether the QTLs are present homozygously or heterozygously in the genome of such a cell of the invention. They are advantageously characterized by the presence of the alleles of at least two of the SNPs disclosed above, at least one on chromosome 1 for QTL1 and at least one on chromosome 2 for QTL2. Preferably, at least one of the QTLs of the combination is present homozygously, such that at least one of the resistant allele of the SNPs is present homozygously; the other QTL may be present homozygously or heterozygously.

Cells according to the invention can be any type of *C. sativus* cell, inter alia an isolated cell and/or a cell capable of regenerating a whole *C. sativus* plant, bearing the QTLs of interest.

The present invention is also directed to a tissue culture of non-regenerable or regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls of the invention, and the cells contain the two QTLs of interest, homozygously or heterozygously in their genome conferring when combined ToLCNDV tolerance, especially when at least one the QTLs of the combination is present homozygously.

The tissue culture will preferably be capable of regenerating plants having the physiological and morphological characteristics of the foregoing cucumber plant, and of regenerating plants having substantially the same genotype as the foregoing cucumber plant. The present invention also provides cucumber plants regenerated from the tissue cultures of the invention.

The invention also provides a protoplast of the plant defined above, or from the tissue culture defined above, said protoplast containing the QTLs conferring the improved phenotype of the invention.

According to still another embodiment of the invention, the plants, cells or seeds of the invention comprise a further QTL on chromosome 4, improving the level of ToLCNDV tolerance. This further QTL on chromosome 4 is preferably characterized by a marker associated to this QTL, preferably allele A of SNP marker CU-0000290 (SEQ ID NO:28). The QTL on chromosome 4 is preferably chosen from the ones present in the genome of seeds of TOCUR6080 on chromosome 4.

According to another aspect, the present invention is also directed to the use of a cucumber plant of the invention, preferably comprising homozygously the QTLs of the invention, as a breeding partner in a breeding program for obtaining *C. sativus* plants having ToLCNDV tolerance. Indeed, such a breeding partner harbors, preferably homozygously in its genome the QTLs conferring the tolerance of interest. By crossing this plant with a cucumber plant, especially a line, it is thus possible to transfer the two QTLs of the present invention conferring the desired phenotype, to the progeny. A plant according to the invention can thus be used as a breeding partner for introgressing QTLs conferring the desired ToLCNDV tolerance into a *C. sativus* plant or germplasm. Although a plant or seed bearing the QTLs of interest heterozygously, can also be used as a breeding partner as detailed above, the segregation of the phenotype is likely to render the breeding program more complex.

The improved phenotype of the invention is tolerance to ToLCNDV.

The introgressed QTLs will advantageously be introduced into varieties that contain other desirable genetic traits such as resistance to others diseases or pest, early fruit maturation, drought tolerance, fruit shape, and the like.

The invention is also directed to the same use with plants or seed of TOCUR6080, deposited at the NCIMB under the accession number NCIMB 43427. Said plants are also suitable as introgression partners in a breeding program aiming at conferring the desired phenotype to a *C. sativus* plant or germplasm.

In such a breeding program, the selection of the progeny displaying the desired phenotype, or bearing the QTLs linked to ToLCNDV tolerance can advantageously be carried out on the basis of the alleles of the SNP markers, especially the SNP markers of the invention.

A progeny of the plant is preferably selected on the presence of at least one of the following alleles; allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168 and allele G of CU-0001983 for QTL1 on chromosome 1 and at least one of allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479 for QTL2 on chromosome 2. The progeny is advantageously selected on the basis of the presence of at least one of said alleles for the markers on chromosome 1 and at least one of said alleles for the markers on chromosome 2.

The progeny of the plant is preferably selected on the presence of the same allele on both homologues of each chromosome, for at least one of the SNPs, which is thus present homozygously for a diploid plant.

The selection can alternatively be made on the basis of the presence of any one of the alleles of the 27 SNPs of the invention linked to the ToLCNDV tolerance or a combination of these alleles. According to such an embodiment, the selection can be made on the presence of at least 1 SNP allele for QTL1 and at least one SNP allele for QTL2 or at least two SNP alleles for QTL1 and at least two SNP alleles for QTL2, or any other combinations. The selection of the progeny is preferably made on the basis of two SNPs or more, at least one SNP allele for QTL1 and at least one SNP allele for QTL2, wherein at least one of the SNPs is homozygous.

According to a distinct embodiment, the progeny may also be selected on the basis of the additional presence of allele A of CU-0000290, on chromosome 4.

Such selection will be made on the presence of the alleles of interest in a genetic material sample of the plant to be selected. The presence of these alleles indeed confirms the presence of QTLs of the invention at the loci defined by said SNPs. Moreover, further to point mutation or recombination event, it is conceivable that at least 1 or 2 of these alleles is lost, the remaining of the chromosomal fragment bearing the QTLs of interest still conferring the phenotype of interest.

A plant according to the invention, or grown from a seed as deposited under accession number NCIMB 43427, is thus particularly valuable in a marker assisted selection for obtaining commercial cucumber lines and varieties, having the improved phenotype of the invention, namely ToLCNDV tolerance.

The invention is also directed to the use of said plants in a program aiming at identifying, sequencing and/or cloning the genetic sequences conferring the desired phenotype.

Any specific embodiment described for the previous aspects of the invention is also applicable to this aspect of the invention, especially with regard to the features of the QTLs conferring the phenotype of interest.

According to a still another aspect, the invention also concerns methods or processes for the production of *C. sativus* plants, especially *C. sativus* var *sativus*, inter alia cultivated cucumbers, having the desired phenotype, especially commercial plants and inbred parental lines. The present invention is indeed also directed to transferring the two QTLs of the invention conferring the ToLCNDV tolerance when present in combination and at least one being homozygous, to other cucumber varieties, or other species or inbred parental lines, and is useful for producing new types and varieties of cucumber.

A method or process for the production of a plant having these features may comprise the following steps:
  a) Crossing a plant grown from a deposited seed NCIMB 43427, or progeny thereof, bearing QTL1 on chromosome 1 and QTL2 on chromosome 2, conferring ToLCNDV tolerance when present in combination, and an initial *C. sativus* plant, preferably devoid of said QTLs, b) Selecting one plant in the progeny thus obtained, bearing the QTL1 and QTL2 of the present invention;
  c) Optionally self-pollinating one or several times the plant obtained at step b) and selecting in the progeny thus obtained a plant having tolerance to ToLCNDV.

Alternatively, the method or process may comprise instead of step a) the following steps:
  a1) Crossing a plant corresponding to the deposited seeds (NCIMB 43427), or progeny thereof, bearing QTL1 and QTL2 conferring ToLCNDV tolerance when present in combination, and an initial *C. sativus* plant, preferably devoid of said QTLs,
  a2) Increasing the F1 hybrid by means of selfing to create F2 population.

In the above methods or processes, SNPs markers are preferably used in steps b) and/or c), for selecting plants bearing sequences conferring the tolerance phenotype of interest.

The SNP markers are preferably one or more of the 27 SNP markers of the invention, including all combinations thereof as mentioned elsewhere in the present application, especially two SNP markers, at least one on chromosome 1 for QTL1 and at least one on chromosome 2 for QTL2. By selecting a plant on the basis of the allele of one or more SNPs, it is to be understood that the plant is selected as having tolerance to the ToLCNDV, or as having at least one of QTL1 or QTL2, with respect to the initial plant, when the allele of the SNP(s) is (are) the allele corresponding to the allele of the tolerant parent for this SNP and not the allele of the initial *C. sativus* plant. Those alleles for the 27 SNPs of the invention have already been detailed in this application.

For example, a plant can be selected as having the improved phenotype of the invention, when allele A of CU-0002031, allele A of CU-0000366 or allele A of CU-0000744 is detected, in combination with detection of allele A of CU-0002682 or allele A of CU-0005012, e.g. allele A of CU-0000744 in combination with allele A of CU-0005012.

Preferably, the *C. sativus* plant of step a) is an elite line, used in order to obtain a plant with commercially desired traits or desired horticultural traits.

A method or process as defined above may advantageously comprise backcrossing steps, preferably after step c), in order to obtain plants having all the characterizing features of *C. sativus* plants, especially *C. sativus.* var *sativus*. Consequently, a method or process for the production of a plant having these features may also comprise the following additional steps:

d) Backcrossing the tolerant plant selected in step b) or c) with a *C. sativus* plant;

e) Selecting a plant bearing QTL1 and QTL2 of the present invention.

The plant used in step a), namely the plant corresponding to the deposited seeds can be a plant grown from the deposited seeds; it may alternatively be any plant according to the 1$^{st}$ aspect of the invention, bearing the combination of QTLs conferring the phenotype, preferably bearing at least one those two QTLs homozygously and preferably both QTLs homozygously.

At step e), SNPs markers can be used for selecting plants having an improved tolerance to ToLCNDV, with respect to the initial plant. The SNP markers are those of the invention, as described in the previous sections.

According to a preferred embodiment, the method or process of the invention is carried out such that, for at least one of the selection steps, namely b), c) and/or e), the selection is based on the detection of at least one of the tolerance alleles reported in tables 3-5.

It is to be noted that, when plants having the improved phenotype, and bearing homozygously at least one of the 2 QTLs, are to be selected, the selection is to be made on the basis of one or more the SNPs of the invention, on the presence of the alleles representative of the QTLs, namely the alleles found in the tolerant parent, coupled to the absence of the alleles representative of the recurrent *C. sativus* parent.

The plant selected at step e) is preferably a cultivated or commercial plant, especially a plant having marketable fruit in normal culture conditions, e.g. 50% of the fruits are at least more than 10 cm long at full maturity, preferably more than 15 or 20 cm at full maturity. The harvested fruits have a green skin color, they preferably have an elongated form.

Preferably, steps d) and e) are repeated at least twice and preferably three times, not necessarily with the same *C. sativus* plant. Said *C. sativus* plant is preferably a breeding line.

Resistance to potyviruses and/or powdery mildew may additionally be selected, at each selection step of the processes disclosed above.

Additionally, the selection may also take account of the proportion of gynoecious flowers, wherein gynoecious plants, or monoecious plants having at least 50%, preferably at least 70% or 80% gynoecious flowers, are selected.

It is also preferred that the selected plant has a number of primary branches which is 4 or less than 4, more preferably 3 or less, e.g. 2, most preferably a plant having only one primary branch.

The self-pollination and backcrossing steps may be carried out in any order and can be intercalated, for example a backcross can be carried out before and after one or several self-pollinations, and self-pollinations can be envisaged before and after one or several backcrosses.

The selection of the progeny having the desired improved phenotype can also be made on the basis of the comparison of the ToLCNDV tolerance from the *C. sativus* parent, through protocols as disclosed inter alia in the examples.

The method used for allele detection can be based on any technique allowing the distinction between two different alleles of a SNP, on a specific chromosome.

The present invention also concerns a plant obtained or obtainable by such a method. Such a plant is indeed a *C. sativus* plant having the improved phenotype according to the first aspect of the invention.

The invention is also directed to a method for obtaining cultivated or commercial cucumber plants or inbred parental lines thereof, having the desired improved phenotype, corresponding to an improved tolerance to the ToLCNDV with respect to an initial commercial *C. sativus* plant, comprising the steps of:

a) Backcrossing a plant obtained by germinating a deposited seed TOCUR6080 NCIMB accession number 43427, or progeny thereof, bearing QTL1 and QTL2 conferring ToLCNDV tolerance when present in combination, with a commercial *C. sativus* plant, b) Selecting a plant bearing QTL1 and QTL2.

Preferably, the selection is made on the basis of one or more, preferably at least two of the 27 SNPs of the invention, as detailed for the other methods of the invention. A selection on the basis of allele A of CU-0000290 may also be added and/or a selection on the basis of the proportion of gynoecious flowers, preferably at least 50%, 70%, 80%, or 100%. A selection on the number of primary branches may also be added, namely selection of plants having less than 4 primary branches, preferably plants having less than 3 primary branches, and most preferably plants having only one primary branch.

According to a preferred embodiment, the progeny bearing QTL1 and QTL2 comprises at least one of them at the homozygous state.

The present invention is also directed to a *C. sativus* plant and seed obtainable by any of the methods and processes disclosed above. The seed of such *C. sativus* are preferably coated or pelleted with individual or combined active species such as plant nutrients, enhancing microorganisms, or products for disinfecting the environment of the seeds and plants. Such species and chemicals may be a product that promotes the growth of plants, for example hormones, or that increases their resistance to environmental stresses, for example defense stimulators, or that stabilizes the pH of the substrate and its immediate surroundings, or alternatively a nutrient. They may also be a product for protecting against agents that are unfavorable toward the growth of young plants, including herein viruses and pathogenic microorganisms, for example a fungicidal, bactericidal, hematicidal, insecticidal or herbicidal product, which acts by contact, ingestion or gaseous diffusion; it is, for example, any suitable essential oil, for example extract of thyme. All these products reinforce the resistance reactions of the plant, and/or disinfect or regulate the environment of said plant. They may also be a live biological material, for example a nonpathogenic microorganism, for example at least one fungus, or a bacterium, or a virus, if necessary with a medium ensuring its viability; and this microorganism, for example of the *pseudomonas, bacillus, trichoderma, clonostachys, fusarium, rhizoctonia*, etc. type stimulates the growth of the plant, or protects it against pathogens.

In all the previous methods and processes, the identification of the plants bearing the QTLs responsible for the improved tolerance to the ToLCNDV could be done by the detection of at least one of the alleles linked with each of the QTLs, but also in combination with the absence of the other allelic form of the SNPs of the present invention, in order to confirm the homozygous state of at least one of the QTL. As such, the identification of a plant bearing homozygously QTL1 of the present invention will be based on the identification of allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168 and allele G of CU-0001983, as well as the absence of the other allele for these SNPs. Similarly, the identification of a plant bearing homozygously QTL2 of the present invention will be based on the identification of allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479 as well as the absence of the other allele for these SNPs.

The invention is also directed to the use of the information provided herewith by the present inventors, namely the existence of 2 QTLs, present in the deposited seeds of TOCUR6080 (NCIMB accession number 43427), and conferring the improved phenotype to *C. sativus* plants when present in combination, and the disclosure of molecular markers associated to these QTLs. This knowledge can be used inter alia for precisely mapping the QTLs, for defining their sequences, for identifying cucumber plants comprising the QTLs conferring the improved phenotype and for identifying further or alternative markers associated to these QTLs. Such further markers are characterized by their location, namely close to the 27 markers disclosed in the present invention, and by their association with the phenotype of interest, revealed by the invention, namely tolerance to ToLCNDV.

The invention is thus also directed to a method for identifying, detecting and/or selecting *C. sativus* plants having the QTLs of the present invention as found in the genome of the seeds of TOCUR6080 (NCIMB accession number 43427), said QTLs conferring an improved ToLCNDV tolerance with respect to a corresponding plant devoid of said QTLs, the method comprising the detection of at least one of the following markers: allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168 and allele G of CU-0001983, in combination with at least one of the following markers: allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479 in a genetic material sample of the plant to be identified and/or selected.

The invention is also directed to a method for detecting or selecting *C. sativus* plants having QTLs conferring ToLCNDV tolerance and having at least one of the alleles mentioned above on chromosome 1 in combination with at least one of the markers mentioned above on chromosome 2, wherein the detection or selection is made on condition of ToLCNDV infection comprising inoculation of ToLCNDV on the plants to be tested, such as artificial inoculation or natural infection by ToLCNDV.

The invention is also directed to a method for detecting and/or selecting a *C. sativus* plant, especially *C. sativus* var *sativus*, inter alia cultivated cucumber, having at least one of the QTLs of the invention, comprising the detection of at least one of the alleles mentioned above for the markers on chromosome 1; or at least one of the alleles mentioned above for the markers on chromosome 2.

The method is particularly adapted in a breeding program with TOCUR6080 (NCIMB accession number 43427), as initial parent, or progeny thereof, comprising the QTLs of the invention conferring ToLCNDV tolerance, wherein the detection and/or selection is made on conditions comprising infestation by ToLCNDV and wherein said introgressed sequences confer tolerance to ToLCNDV and have at least one of the following alleles: allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168 and allele G of CU-0001983, in combination with at least one of the following markers: allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479.

The invention also relates to a method for detecting and/or selecting *C. sativus* plants having the two QTLs of the present invention conferring the improved phenotype, on the basis of the allele detection of at least one SNP chosen amongst the 12 SNPs of QTL1 and at least one of the 15 SNPs of QTL2. A plant will be selected for the presence of QTL1 if at least one, preferably at least 2, 3, 5, 8, 10 or the 12 SNPs of QTL1 have the allele representative of the ToLCNDV tolerance. A plant will be selected for the presence of QTL2 if at least one, preferably at least 2, 3, 5, 8, 10, 12 or the 15 SNPs of QTL2 have the allele representative of the ToLCNDV tolerance.

The invention is further directed to a method for detecting and/or selecting *C. sativus* plants, especially *C. sativus* var *sativus*, inter alia cultivated cucumbers, having one or the two QTLs of the present invention conferring the improved phenotype, on the basis of the detection of any molecular marker revealing the presence of said QTLs. Indeed, now that the QTLs of the present invention have been identified by the present inventors, the identification and then the use of molecular markers, in addition to the 27 SNPs of the invention could be done by the skilled artisan. The QTLs themselves may be characterized by the presence of at least one of the 27 SNPs of the invention, but they may also be identified through the use of different, alternative markers. Also included in the present invention are thus methods and uses of any such molecular markers for identifying one or the two QTLs of the invention in a cucumber genome, wherein said QTLs confer improved tolerance to ToLCNDV with respect to a corresponding plant devoid of said QTLs wherein said QTLs are characterized by the presence of at least one of the following SNPs: CU-0002005, CU-0000824, CU-0001679, CU-0000195, CU-0000697, CU-0000649, CU-0002031, CU-0000366, CU-0000554, CU-0000744, CU-0006168 and CU-0001983 for QTL1 on chromosome 1 and at least one of CU-0000463, CU-0001997, CU-0001204, CU-0003652, CU-0002682, CU-0005012, CU-0001371, CU-0002276, CU-0002479, CU-0006476, CU-0003181, CU-0001663, CU-0001531, CU-0001495 and CU-0006479 for QTL2 on chromosome 2.

Are also included methods and uses of any such alternative molecular markers for identifying the QTLs of the invention in a cucumber genome, wherein said QTLs confer tolerance to ToLCNDV wherein said QTLs are characterized by the presence of at least one of the 12 tolerance alleles of the 12 SNPs of table 3, in combination with at least one of the 15 tolerance alleles of the 15 SNPs of table 4.

The invention also concerns a method for detecting and/or selecting cucumber plants having at least one of QTL1 and QTL2 as defined previously, conferring tolerance to ToLCNDV when present in combination, said method comprising:
  a) Assaying cucumber plants for the presence of at least one genetic marker genetically linked or associated to QTL1 or QTL2 involved in tolerance to ToLCNDV,
  b) Selecting a plant comprising the genetic marker and the linked or associated QTL1 or QTL2 involved in tolerance to ToLCNDV,
wherein the QTL and the genetic marker are to be found in the chromosomal region delimited on chromosome 1 by CU-0002005 and CU-0001983 or in the chromosomal region delimited on chromosome 2 by CU-0000463 and CU-0006479.

By association, or genetic association, and more specifically genetic linkage, it is to be understood that a genetic polymorphism of the marker (i.e. a specific allele of the SNP marker) and the phenotype of interest occur simultaneously, i.e. are inherited together, more often than would be expected by chance occurrence, i.e. there is a non-random association of the allele and of the genetic sequences responsible for the phenotype, as a result of their proximity on the same chromosome.

A molecular marker of the invention, either one of 27 markers disclosed above or alternative markers, are inherited with the phenotype of interest in preferably more than 90% of the meioses, preferably in more than 95%, 96%, 98% or 99% of the meioses.

The definition and preferred features of the QTLs are as defined in other sections of the present specification.

Any of the methods of the invention may further comprise the detection of a further QTL on chromosome 4, improving the level of ToLCNDV tolerance. This further QTL on chromosome 4 is preferably characterized by a marker associated to this QTL, preferably allele A of SNP marker CU-0000290 (SEQ ID NO: 28).

The invention thus concerns the use of one or more molecular markers, for fine-mapping or identifying a QTL in the cucumber genome, said QTL participating to the improved phenotype of the invention, wherein said one or more markers is/are localized in one of the following chromosomal regions:
  in the chromosomal region delimited on chromosome 1 by CU-0002005 and CU-0001983,
  in the chromosomal region delimited on chromosome 2 by CU-0000463 and CU-0006479,
  at less than 2 megabase units from the locus of one of the 27 SNP markers of the invention, namely CU-0002005, CU-0000824, CU-0001679, CU-0000195, CU-0000697, CU-0000649, CU-0002031, CU-0000366, CU-0000554, CU-0000744, CU-0006168, CU-0001983, CU-0000463, CU-0001997, CU-0001204, CU-0003652, CU-0002682, CU-0005012, CU-0001371, CU-0002276, CU-0001479, CU-0006476, CU-0003181, CU-0001663, CU-0001531, CU-0001495 and CU-0006479.

According to a preferred embodiment, said one or more markers are in the chromosomal region delimited by CU-0002005 and CU-0001983, preferably by CU-0002005 and CU-0006168, more preferably by CU-0000649 and CU-0000554, and even more preferably by CU-0002031 and CU-0000366, on chromosome 1. According to another embodiment, said one or more markers are in the chromosomal region delimited by CU-0000463 and SNP CU-0006479, preferably by CU-0000463 and CU-0002276, more preferably by CU-0003652 and CU-0001371, and even more preferably by CU-0002682 and CU-0005012, on chromosome 2.

Said one or more molecular marker(s) is/are moreover preferably associated, with a p-value of 0.05 or less, with at least one of the following SNP alleles: allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168 and allele G of CU-0001983, on chromosome 1, and allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479 on chromosome 2. Preferably, there are at least two markers, one associated with an allele on chromosome 1 and one associated with an allele on chromosome 2.

The molecular marker is preferably a SNP marker. It is more preferably at less than 1 megabase from the locus of at least one of the 27 SNPs of the invention.

The QTL are to be found in the deposited seeds NCIMB 43427.

The p-value is preferably less than 0.01.

The invention is also directed to the use of at least one of the 27 SNPs of the invention, associated with QTLs on chromosome 1 (SEQ ID No: 1-12) and chromosome 2 (SEQ ID No: 13-27) conferring, when combined, ToLCNDV tolerance, for identifying alternative molecular markers associated with said QTLs, wherein said alternative molecular markers are:
  in the chromosomal region delimited on chromosome 1 by CU-0002005 and CU-0001983,
  in the chromosomal region delimited on chromosome 2 by CU-0000463 and CU-0006479,
  at less than 2 megabase units from the locus of one of the 27 SNP markers of the invention.

According to a preferred embodiment, said alternative markers are in the chromosomal region delimited by CU-0002005 and CU-0006168, or by CU-0000649 and CU-0000554, or by CU-0002031 and CU-0000366 on chromosome 1, or by CU-0000463 and CU-0002276, by CU-0003652 and CU-0001371, or by CU-0002682 and CU-0005012, on chromosome 2.

The alternative molecular markers are preferably associated with said QTL(s) with a p-value of 0.05 or less, preferably less than 0.01. The QTLs are to be found in the deposited seeds NCIMB 43427.

The QTLs on chromosomes 1 and 2 mentioned above, conferring the ToLCNDV tolerance according to the invention, are the QTLs present in TOCUR6080 (NCIMB 43427).

Genetic association or linkage is as defined above; preferably the association or linkage is with a p-value of preferably less than 0.05, and most preferably less than 0.01 or even less.

A molecular marker and the tolerance phenotype are inherited together in preferably more than 90% of the meioses, preferably more than 95%.

The molecular markers according to this aspect of the invention are most preferably SNP. They are more preferably at less than 1 megabase from the locus of at least one of the 27 SNPs of the invention, preferably at less than 0.5 megabases.

The invention also comprises a method for identifying a molecular marker associated with a QTL participating to ToLCNDV tolerance in cucumbers, as described in the present application, comprising the steps of:
identifying a molecular marker in the chromosomal region delimited on chromosome 1 by SNP markers CU-0002005 (SEQ ID NO:1) and CU-0001983 (SEQ ID NO:12) or in the chromosomal region delimited on chromosome 2 by SNP markers CU-0000463 (SEQ ID No. 13) and CU-0006479 (SEQ ID NO:27) or at less than 2 megabase units from the locus of SNP CU-0000744 or CU-0005012, preferably less than 0.5 megabase units; and
determining whether an allele or state of said molecular marker is associated with the phenotype of tolerance to ToLCND virus in a segregating population issued from a plant exhibiting tolerance to ToLCND virus, for example in a segregating population issued from a plant corresponding to the deposited seeds.

The invention is also directed to the use of a molecular marker for identifying or selecting a cucumber plant comprising, in its genome, a QTL conferring ToLCNDV tolerance to *C. sativus* var *sativus* plants when present in combination with another QTL, wherein said marker is localized in the chromosomal region delimited on chromosome 1 by the SNP markers CU-0002005 and CU-0001983, or in the chromosomal region delimited on chromosome 2 by the SNPs CU-0000463 and CU-0006479 or at less than 2 megabase unit from the locus of at least one of the 27 SNP markers of the invention; and wherein said molecular marker is associated with at least one of the following SNP alleles: allele A of CU-0002005, allele G of CU-0000824, allele A of CU-0001679, allele G of CU-0000195, allele A of CU-0000697, allele G of CU-0000649, allele A of CU-0002031, allele A of CU-0000366, allele A of CU-0000554, allele A of CU-0000744, allele G of CU-0006168, allele G of CU-0001983, allele A of CU-0000463, allele A of CU-0001997, allele A of CU-0001204, allele A of CU-0003652, allele A of CU-0002682, allele A of CU-0005012, allele A of CU-0001371, allele A of CU-0002276, allele C of CU-0001479, allele A of CU-0006476, allele G of CU-0003181, allele A of CU-0001663, allele A of CU-0001531, allele C of CU-0001495 and allele G of CU-0006479, with a p-value of 0.05 or less, preferably 0.01 or less. The ToLCNDV tolerance is conferred when a QTL on chromosome 1 and a QTL on chromosome 2 are present, preferably at least one being present homozygously.

The molecular marker to be used according to this embodiment is obtainable inter alia by the method for identifying further or alternative molecular markers, as disclosed above. The molecular marker is preferably a SNP marker. They are more preferably at less than 1 megabase from the locus of at least one of the 27 SNPs of the invention.

According to still another aspect, the invention is also directed to a method for genotyping a plant, preferably a *C. sativus* plant or cucumber germplasm, for the presence of at least one genetic marker associated with tolerance to ToLCNDV infection, wherein the method comprises the determination or detection in the genome of the tested plant of a nucleic acid comprising at least one of the markers of the invention, or comprising at least one of the alternative molecular markers as disclosed above. Preferably, the method comprises the step of identifying in a sample of the plant to be tested specific sequences associated with tolerance to ToLCNDV, in nucleic acid comprising at least one of the alleles of the SNPs of the invention, as already disclosed.

The detection of a specific allele of a SNP can be carried out by any method well known to the skilled reader.

In view of the ability of the tolerant plants of the invention to restrict the damages caused by ToLCNDV infection, they are advantageously grown in an environment infested or likely to be infested or infected by ToLCNDV; in these conditions, the resistant or tolerant plants of the invention produce more marketable cucumbers than susceptible plants. The invention is thus also directed to a method for improving the yield of cucumber plants in an environment infested by ToLCNDV comprising growing cucumber plants comprising in their genome a QTL on chromosome 1 in combination with a QTL on chromosome 2, wherein said QTLs are as defined according to the previous aspects of the invention, and conferring to said plants tolerance to ToLCNDV when present in combination. Preferably, at least one of those two QTLs is present homozygously. Still preferably, both QTLs are present homozygously.

Preferably, the method comprises a first step of choosing or selecting a cucumber plant having said QTLs of interest. The method can also be defined as a method of increasing the productivity of a cucumber field, tunnel, greenhouse or glasshouse.

The invention is also directed to a method for reducing the loss on cucumber production in conditions of ToLCNDV infestation or infection, comprising growing a cucumber plant as defined above.

These methods are particularly valuable for a population of cucumber plants, either in a field, in tunnels, greenhouses or in glasshouses.

Alternatively, said methods for improving the yield or reducing the loss on cucumber production may comprise a first step of identifying cucumber plants tolerant to ToLCNDV and comprising in their genome a QTL on chromosome 1 and a QTL on chromosome 2, that confer to said plants when present in combination, tolerance to ToLCNDV, and then growing said tolerant plants in an environment infested or likely to be infested by the virus.

The tolerant plants of the invention are also able to restrict at least partially, the growth of ToLCNDV, thus limiting the infection of further plants and the propagation of the virus. Accordingly, the invention is also directed to a method of protecting a field, tunnel, greenhouse or glasshouse, or any other type of plantation, from ToLCNDV infestation, or of at least limiting the level of infestation by ToLCNDV of said field, tunnel, greenhouse or glasshouse or of limiting the spread of ToLCNDV in a field, tunnel, greenhouse or glasshouse, especially in glasshouse. Such a method preferably comprises the step of growing a tolerant plant of the invention, i.e. a plant comprising in its genome a QTL1 on chromosome 1 and a QTL2 on chromosome 2, conferring to said plant, when combined, tolerance to ToLCNDV.

The invention also concerns the use of a plant tolerant to ToLCNDV for controlling ToLCNDV infection or infestation in a field, tunnel, greenhouse or glasshouse, or other plantation; such a plant is a plant of the invention, comprising in its genome a QTL1 and a QTL2, as defined above, on chromosomes 1 and 2 respectively. According to this use, the plants of the invention are therefore used for protecting a field, tunnel, greenhouse or glasshouse from ToLCNDV infestation.

LEGEND OF FIGURES

FIG. 1 illustrates the distribution of the level of ToLCNDV resistance/tolerance of F2 plants from the cross CUC29×CUC01, at two different times (1 Ev at 6 weeks DPI and 2 Ev at 8 weeks DPI) as well as the evolution of the symptoms (AUDPC: area under the disease progress curve to quantify disease progress).

R stands for resistant or tolerant, S for susceptible. N is the number of plants.

EXAMPLES

Figure 1:
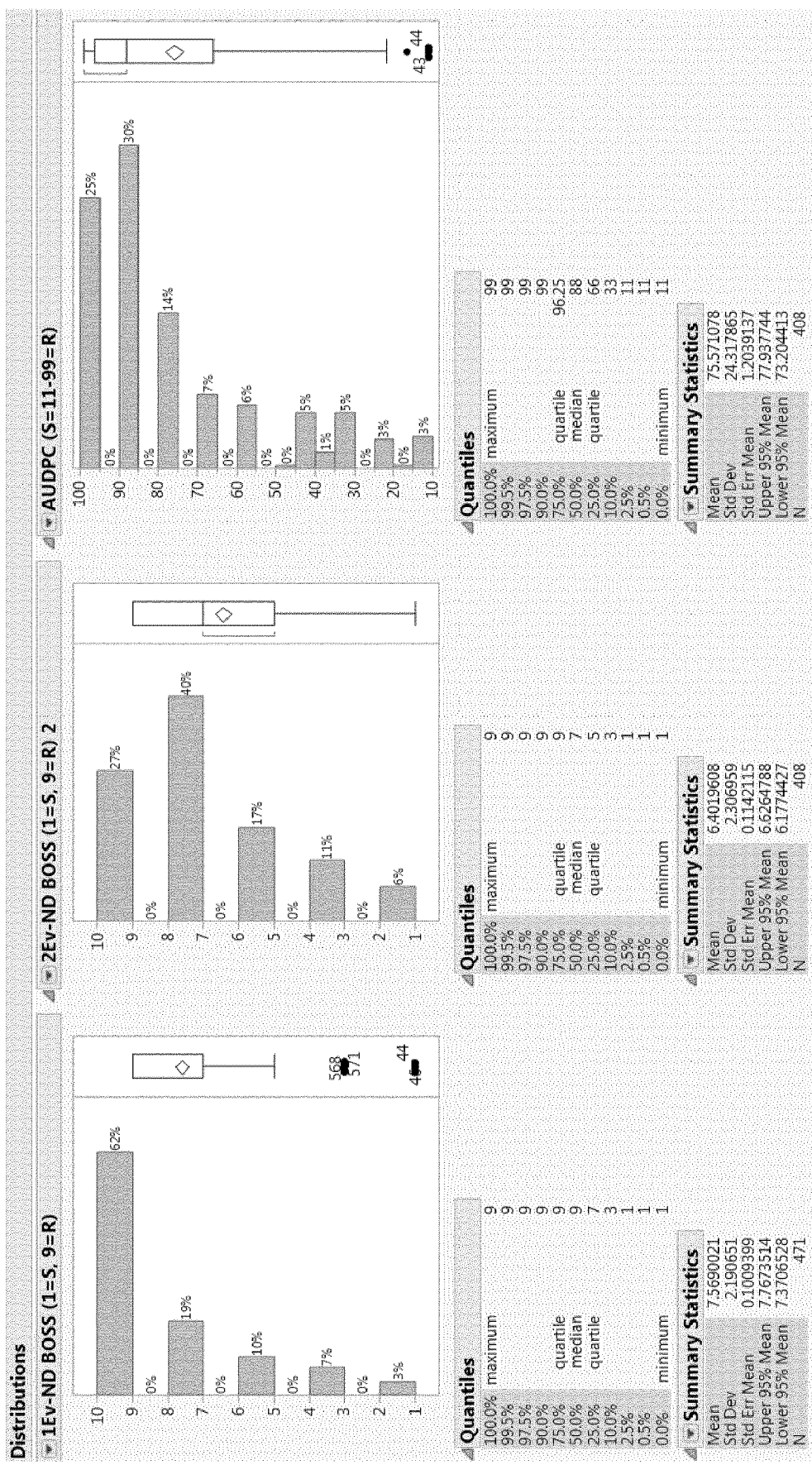

Example 1: Adjusting Phenotyping Protocol and Screening for Resistant Plants

During Fall 2015, a trial was conducted, aiming to find ToLCNDV resistance leads in cucumber. After screening for potential leads, 34 genotypes were selected (5 commercial varieties, 2 Long European Type breeding lines that were observed in recent years during the breeding program and 27 landraces). Additional 2 commercial hybrids were tested as susceptible controls (according to previous observation at the breeding program).

The trial was infected by whiteflies *Bemisia tabaci* (at least 50 females/leaf/plant), on September 6$^{th}$-September 8$^{th}$. All whiteflies acquired ToLCNDV from infected and symptomatic squash plants. The inoculation process was as follows:

Squash plants with whiteflies and ToLCNDV symptoms were used as a source of inoculum. Presence of ToLCNDV and absence of CYSDV and CVYV were verified. 20 plants of squash were grown and exposed to the infected plants as described before, for 6 weeks, inside an insect proof cage.

The plants of the cucumber genotype trial were then sown separately, and after 14 days were put together, in the cage with the infected squash plants.

Each plant of the trial has 20-50 adult whiteflies for 48-72 hours. The *Bemisia tabaci* were removed using pesticides.

The plants of the trial were then transplanted on September 9$^{th}$ in the greenhouse.

Evaluation was made 6 weeks post infection, on November 22$^{nd}$.

The selected genotypes were:

TABLE 1

| Internal code | Botanical species |
| --- | --- |
| CUC01 | *C. sativus* |
| CUC02 | *C. sativus* |
| CUC03 | *C. sativus* |
| CUC04 | *C. sativus* |
| CUC05 | *C. sativus* |
| CUC06 | *C. sativus* |
| CUC07 | *C. sativus* |
| CUC09 | *C. sativus* |
| CUC10 | *C. sativus* |
| CUC11 | *C. sativus* |
| CUC12 | *C. sativus* |
| CUC13 | *C. sativus* |
| CUC14 | *C. sativus* |
| CUC15 | *C. sativus* |
| CUC16 | *C. sativus* |
| CUC17 | *C. sativus* |
| CUC18 | *C. sativus* |
| CUC19 | *C. sativus* |
| CUC20 | *C. sativus* var. *hardwickii* |
| CUC21 | |
| CUC22 | *C. sativus* |
| CUC23 | *C. sativus* |
| CUC24 | *C. sativus* |
| CUC25 | *C. sativus* |
| CUC26 | *C. sativus* |
| CUC27 | *C. sativus* |
| CUC28 | *C. sativus* |
| CUC29 | *C. sativus* |
| CUC30 | *C. sativus* |
| CUC31 | *C. sativus* |
| CUC32 | *C. sativus* |
| CUC34 | *C. sativus* var. *hardwickii* |
| SAT01 | *C. sativus* |
| SAT02 | *C. sativus* |

The plants corresponding to the genotype SAT01 did not germinate and genotype SAT02 had bad germination. For that reason, the infection quality is not certain for SAT02 at the time of infection. The trial was designed as a complete block design (4 blocks) where each block contains 3-5 plants of each genotype (15-20 plants per accession).

The phenotypic evaluation was done according to four disease index:
1—very susceptible
2—susceptible
3—Intermediate (minor disease symptoms)
4—resistant (No disease symptoms)

TABLE 2

| Accession | Phenotype | | | | Total plant number |
| --- | --- | --- | --- | --- | --- |
| | 1 (S) | 2 (I-S) | 3 (I-R) | 4 (R) | |
| CUC01 | 20 | 0 | 0 | 0 | 20 |
| CUC02 | 1 | 0 | 16 | 1 | 18 |
| CUC03 | 7 | 9 | 2 | 0 | 18 |
| CUC04 | 12 | 6 | 0 | 0 | 18 |
| CUC05 | 6 | 11 | 0 | 0 | 17 |
| CUC06 | 11 | 7 | 0 | 0 | 18 |
| CUC07 | 5 | 5 | 0 | 0 | 10 |
| CUC09 | 14 | 4 | 0 | 0 | 18 |
| CUC10 | 9 | 10 | 0 | 0 | 19 |
| CUC11 | 11 | 6 | 2 | 0 | 19 |

TABLE 2-continued

| Accession | Phenotype | | | | Total plant number |
|---|---|---|---|---|---|
| | 1 (S) | 2 (I-S) | 3 (I-R) | 4 (R) | |
| CUC12 | 19 | 0 | 0 | 0 | 19 |
| CUC13 | 9 | 5 | 0 | 0 | 14 |
| CUC14 | 19 | 0 | 0 | 0 | 19 |
| CUC15 | 14 | 4 | 0 | 0 | 18 |
| CUC16 | 9 | 6 | 0 | 0 | 15 |
| CUC17 | 0 | 0 | 0 | 0 | 0 |
| CUC18 | 0 | 4 | 1 | 0 | 5 |
| CUC19 | 10 | 10 | 0 | 0 | 20 |
| CUC20 | 11 | 8 | 0 | 0 | 19 |
| CUC21 | 0 | 1 | 1 | 15 | 17 |
| CUC22 | 1 | 0 | 0 | 4 | 5 |
| CUC23 | 15 | 3 | 0 | 0 | 18 |
| CUC24 | 7 | 6 | 1 | 2 | 16 |
| CUC25 | 1 | 1 | 3 | 12 | 17 |
| CUC26 | 6 | 4 | 3 | 6 | 19 |
| CUC27 | 1 | 2 | 3 | 9 | 15 |
| CUC28 | 0 | 8 | 6 | 3 | 17 |
| CUC29 | 0 | 0 | 1 | 17 | 18 |
| CUC30 | 4 | 8 | 0 | 0 | 12 |
| CUC31 | 10 | 2 | 0 | 0 | 12 |
| CUC32 | 13 | 4 | 0 | 0 | 17 |
| CUC34 | 4 | 6 | 0 | 2 | 12 |
| SAT01 | 0 | 0 | 0 | 0 | 0 |
| SAT02 | 0 | 0 | 0 | 18 | 18 |

Further to this trial, seven leads were found, namely CUC21, CUC25, CUC26, CUC27, CUC28, CUC29 and SAT02. No tested commercial varieties were observed as really resistant.

CUC21: 15/17 plants were observed resistant. This line has however many necrotic effects that makes it difficult to be used in breeding program.

SAT02: 18/18 plants were observed resistant; this line had however bad germination, which may have biased the resistance results.

Out of the 5 remaining leads, CUC29, with 17/18 resistant plants, was chosen for further work. Moreover, all the other leads (except CUC29) are segregating and need to be selected and fixed before any further work. CUC29 seems to be fixed for resistance and was thus also chosen for this further reason.

When plants were evaluated 10 weeks post infection (i.e. 4 weeks after the first evaluation), the general findings were:
The susceptible lines continue to express symptoms,
the plants expressing intermediate symptoms (level 3) turned to be symptomless (level 4).

CUC29 (Landrace) was thus confirmed as the more resistant lines; in order to confirm that the tolerance found in CUC02 and in CUC29 was different in nature, a comparison of both genotypes was carried out (see example 3).

Example 2: Creation of a F2 Mapping Population Derived from CUC29×CUC01

An F2 mapping population with CUC01 as susceptible parent were created, namely CUC29 (R parent)*CUC01 (S Parent).

In order to have a more accurate phenotyping data, the mapping population was phenotyped using 5 levels (1=very susceptible, 3=susceptible, 5=intermediate resistant (IR), 7=more resistant than IR but not resistant, 9=resistant).

The phenotypic results on the F2 CUC29×CUC01 are illustrated on FIG. 1. Two different evaluations of the phenotype were carried out, 6 weeks after infection ($1^{st}$ evaluation), and 8 weeks after infection ($2^{nd}$ evaluation). The disease progress is then evaluated on the basis of these two evaluations. For comparison, for the susceptible parent, the mean of the $1^{st}$ evaluation was 5.1; the mean for the $2^{nd}$ evaluation was 4.8 and the mean of the AUDPC was 54.4 (Standard deviation of 13.8), which means that, naturally, more than 40% of the CUC01 susceptible parent show Intermediate resistance/tolerance, under these conditions.

Finally, with a view to comparing CUC02 and CUC29, an equivalent F2 mapping population was also created with CUC02×CUC01 (see example 3).

Example 3: QTL Analysis on the F2 Mapping Population Derived from CUC29×CUC01

A complete QTL analysis was carried out with available SNPs.

A first selection was carried out among the potential SNPs on the basis of their allelic variations between CUC29 and CUC01. The F2 mapping population was finally screened with a set of 27 SNPs, covering all the chromosomes, having the better-log 10 (p-value) or the better $R^2$ value. The SNP markers detection is performed using the KASPar™ technology. KASPar™ primers were designed using PrimerPicker™ tool in KLIMS™ (KBioscience Laboratory Management System) by providing DNA sequences with SNPs. Three primers, A1 (Allele specific primer 1), A2 (Allele specific primer 2), and C (common reverse primer) were designed for each SNP sequence based on KASPar™ chemistry. DNA strand and allele designation and orientation is done according to the TOP/BOT method developed by Illumina:
illumina.com/documents/products/technotes/techno-te_topbot.pdf.

Figure 2:
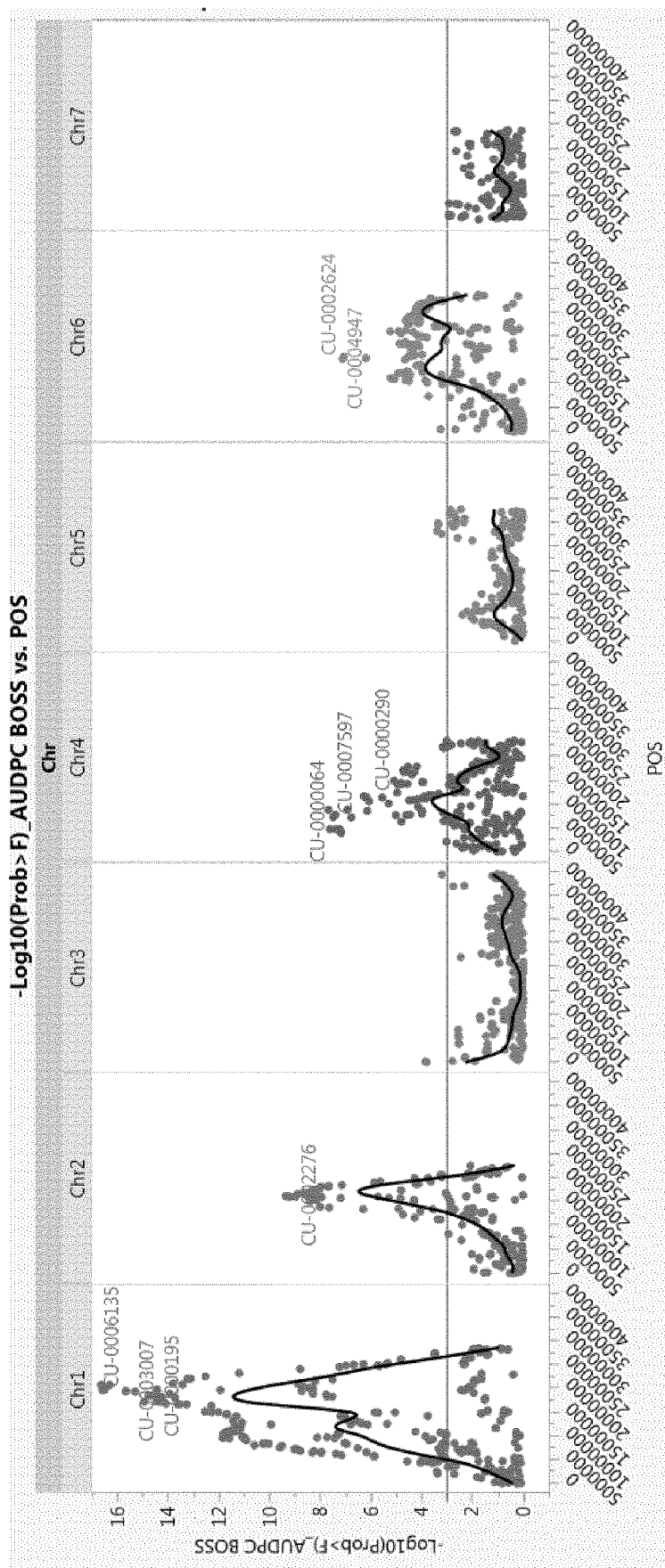
FIG. 2 is the Manhattan plot showing mapping results of F2 population. Vertical axis (y-axis) shows the −log 10 of p-value and horizontal axis (x-axis) represents all SNPs by their positions by chromosomes along the genetic map and 7 chromosomes of cucumber.

The results of the QTL analysis are illustrated on FIG. 2.

The genotypic analysis revealed 2 QTLs linked to the tolerance: The QTL interval on chromosome 1 is between CU-0002005 (pos. 20,879,343) to CU-0006168 (pos. 22,663,842), LOD 3.51 The QTL interval on chromosome 2 is between CU-0000463 (pos. 15,987,817) to CU-0002276 (pos. 16,649,407), LOD 3.02

A third QTL with minor effect was also detected on chromosome 4, at the locus of SNP CU-0000290, positioned on chromosome 4:11,511,634, sequence:

(SEQ ID NO: 28)
TTGGGAATGCAAAACACATCATCGATAACATGTAAGTTTGAAAGTATGAA

ATGTAACCTTCCCCCTACAGATTGCTGCTTAGCTCCATGCATATAGAGTC

[A/G]TCAGTAAACTATATTATACACTCTTTAAGAGTTGCTGCTTCTAGG

CAAACCTTTTGATTGTCTCTATACCCAYCTCTTTTGTCAACAAGGGAACA

CTTAT.

The allele linked to the tolerance is underlined (allele A).

The sequences of the SNPs on chromosomes 1 and 2, including the surrounding sequences, and the position in the cucumber genome (genome v2.0, Chinese Long IL 9930, available at cucurbitgenomics.org/organism/2, based on Huang et al, 2009, and Li et al, 2011) are given in tables 3 and 4 for chromosomes 1 and 2 respectively. Table 5 gives the results of the QTL analysis, namely the value of –Log 10 (Prob>F) and $R^2$ values. The –log 10 (p-value) parameter is indeed an indication of the correlation to the tolerance phenotype (highest values are indicative of a highest correlation) and the $R^2$ value is an indication of the effect of the marker on the phenotype of tolerance to the disease.

A comparison of the F2 mapping population CUC29×CUC01 and CUC02×CUC01 reveals that CUC02 does not comprise the QTL on chromosomes 1 and 2 as described above, especially there is no position on chromosome 2 which is associated with tolerance in F2 mapping population of CUC02.

Example 4: QTL Validation

A new F1 population was made using CUC01×CUC29, Marker-assisted selection (MAS) was done to choose the F1s with the QTL intervals. The relevant F1 were crossed with CUC01 to get BC1F1, MAS was done on the BC1F1 to choose the ones with the QTL intervals. The BC1F1 were selfed to obtain BC1F2, MAS was done on the BC1F2 to choose the ones with the QTL intervals to get BC1F3.

Table 5 gives the results of the QTL analysis, namely the value of –Log 10 (Prob>F) and $R^2$ values for the thus obtained BC1F3.

Given the marker-assisted selection made at the BC1F1 level, and the high number of plants in the BC1F3 population, the p-values and $R^2$ data obtained with this F3 population allow a better definition of the QTLs. The analysis based on this BC1F3 population indeed revealed 2 QTLs linked to the tolerance:

The QTL interval on chromosome 1 is between CU-0002005 (pos. 20,879,343) to CU-0001983 (pos. 23,366,713).

The QTL interval on chromosome 2 is between CU-0000463 (pos. 15,987,817) to CU-0006479 (pos. 17,291,444).

The results with the BC1F3 also confirm the QTL on chromosome 4, around the SNP CU-0000290 at position 11,511,634.

Figure 3:
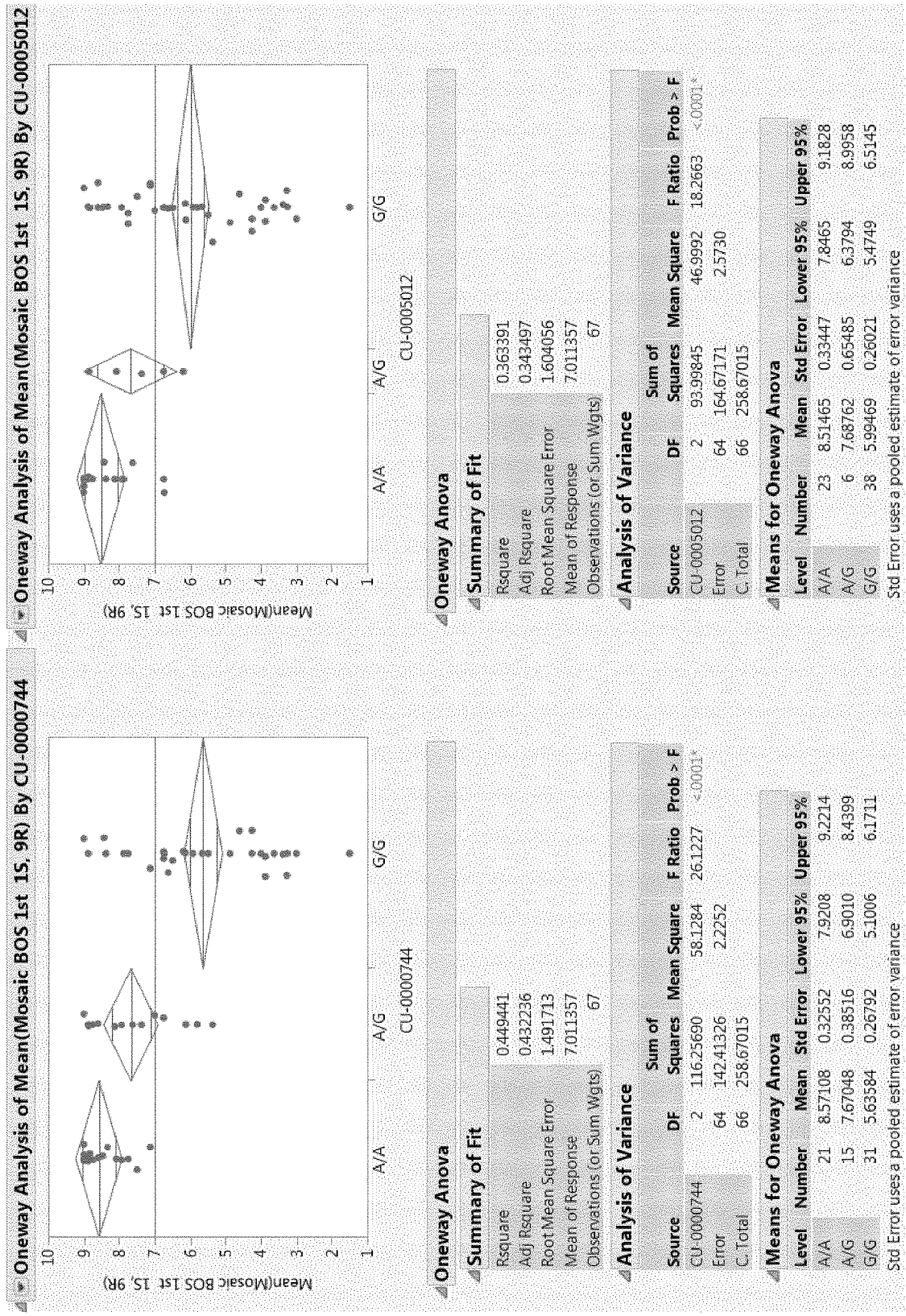
FIG. 3 illustrates correlation between QTL and tolerance (each QTL separately), on the basis of the allele of one SNP for each QTL, namely CU-0000744 for QTL1 and CU-0005012 for QTL2.
Figure 4:
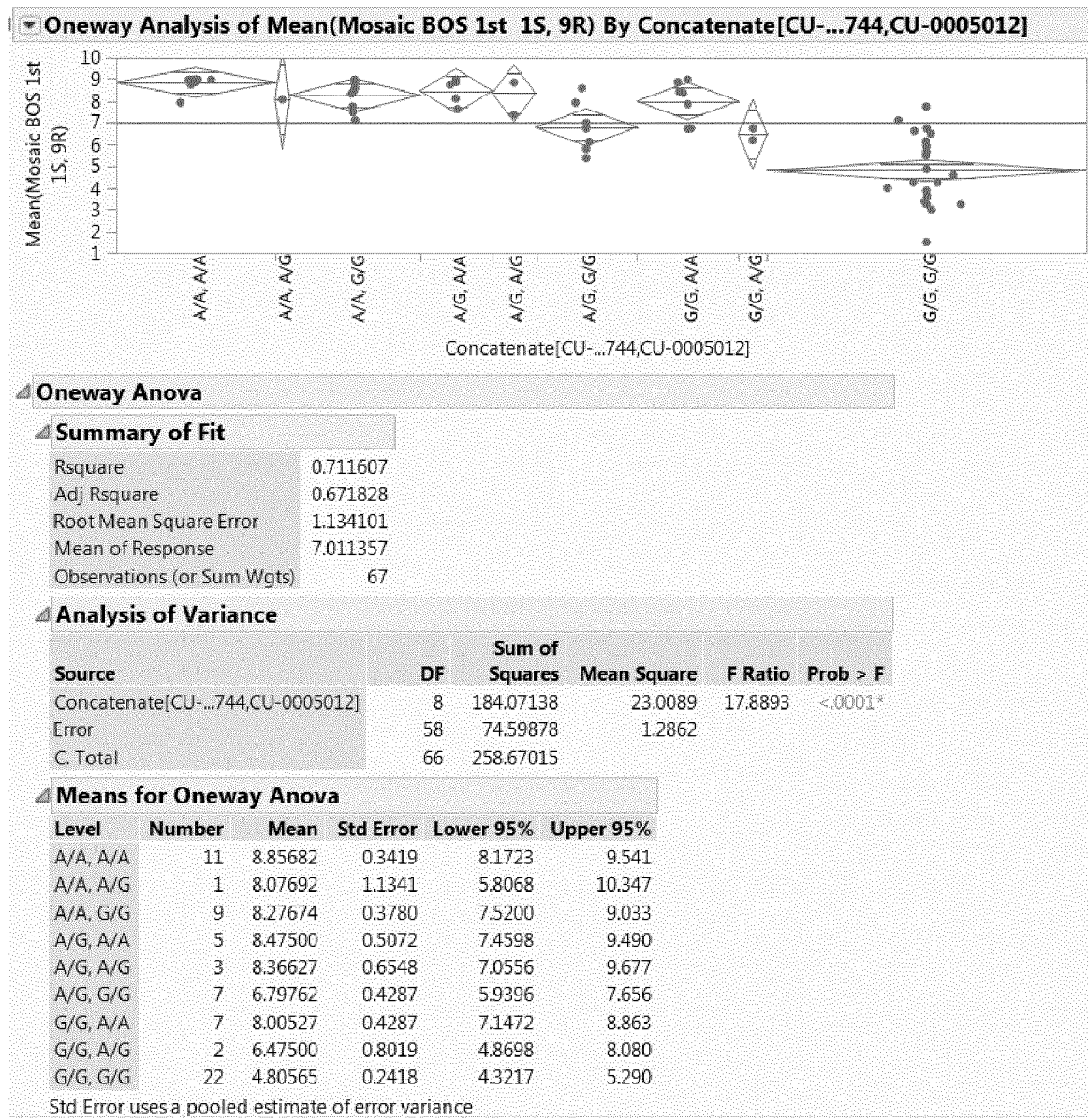
FIG. 4 illustrates correlation of both QTLs combination to the ToLCNDV tolerance, on the basis of the alleles of one SNP for each QTL, namely CU-0000744 for QTL1 and CU-0005012 for QTL2.

The correlation between the QTL and the phenotype of tolerance or resistance is illustrated in FIG. 3, for each QTL independently, and in FIG. 4 for both QTLs in combination.

Seeds corresponding to the BC1F3 were selected on the basis of the homozygous presence of both QTLs and of the QTL on chromosome 4, for seed deposit at the NCIMB under accession number 43427 on Jun. 24, 2019.

Example 5: Androecious/Gynoecious Sex Expression

CUC29 shows androecious sex expression. By doing 2 backcrosses, it is however possible to change the sex expression of a resistant material from androecious to gynoecious. The inventors have illustrated this change through backcrosses with the line CUC01, not having an androecious sex expression.

Figure 5:
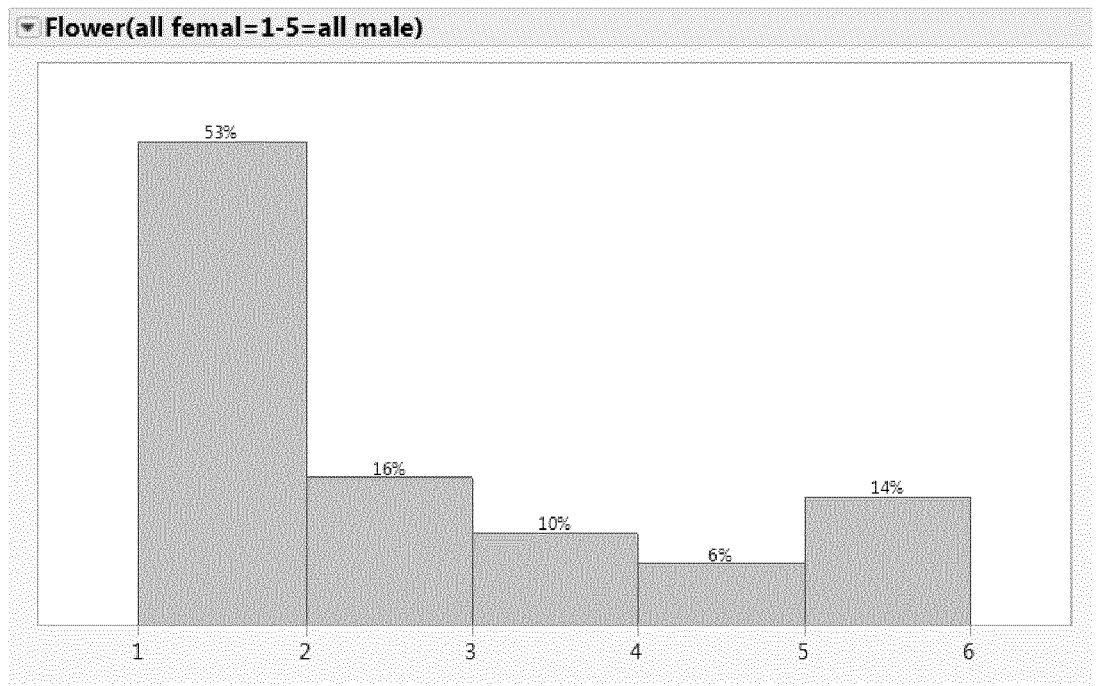
FIG. 5 illustrates the proportion of androecious v. gynoecious sex expression in the F2 of CUC01×CUC29.

FIG. 5 illustrates the androecious/gynoecious sex expression in the F2 of CUC01×CUC29. The androecious/gynoecious sex expression is measured by the respective number of female and male flowers.

Figure 6:
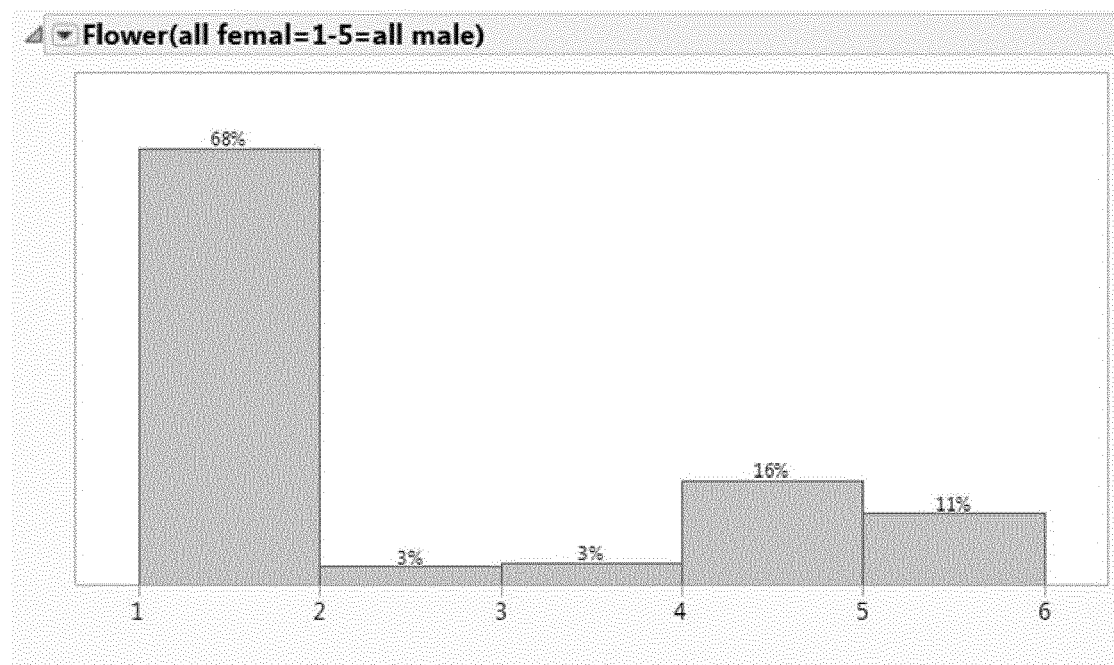
FIG. 6 illustrates the proportion of androecious v. gynoecious sex expression in the BC1F3 of CUC01×CUC29

The same analysis has been carried out on the BC1F3 of CUC01×CUC29; comprising one additional backcross with respect to the F2 of CUC01×CUC29, and the results are illustrated on FIG. 6. As can be observed, the androecious sex expression of the CUC29 parent has been totally changed to a gynoecious sex expression through the two backcrosses.

Example 6: Genetic Modification of Cucumber Seeds by Ethyl Methane Sulfonate (EMS)

Seeds of a cucumber varieties are to be treated with EMS by submergence of approximately 2000 seeds per variety into an aerated solution of either 0.5% (w/v) or 0.7% EMS for 24 hours at room temperature.

Approximately 1500 treated seeds per variety per EMS dose are germinated and the resulting plants are grown, preferably in a greenhouse, to produce seeds.

Following maturation, M2 seeds are harvested and bulked in one pool per variety per treatment. The resulting pools of M2 seeds are used as starting material to identify the individual M2 seeds and the plants with a tolerance to Tomato Leaf curl New Delhi virus.

TABLE 3

SNPs present in the QTL on chromosome 1. The polymorphism is indicated within brackets. The allele representative of the presence of the QTL is underlined in the bracket and reported in the last column (Tolerance T allele). The position is with respect to the cucumber genome as published: genome v2.0, Chinese Long IL 9930, available at cucurbitgenomics.org/organism/2 (based on Huang et al, 2009 and Li et al, 2011).

| SNP_id | Position | SEQ (TOP) | SEQ ID | T allele |
|---|---|---|---|---|
| CU-0002005 | 20879343 | CATGTCTGTCCAAACAACAAAACAGAGAAGCTCAC[A/G]AAGTATAGATAATTAAACAAAGTTTGTTCTCTAAG | 1 | A |
| CU-0000824 | 20885446 | TTACTTTTTGGCTTCAAATTGGTTTGGGGTTGAGA[A/G]CTTTGAATTTCTGTGGCAGTGGGGTGTTAGTGTGT | 2 | G |
| CU-0001679 | 20926977 | CTGATGAAGCATAAAGAATGAGTTACACTTCAGCG[A/C]IITATTACACTAAGAAAATAGTTAAACTTCAAGTCC | 3 | A |
| CU-0000195 | 20933874 | TAGTTATCAATTGGAAGGAACTTGGCGTATCGCTC[A/G]GCCTTCGCTCCTGATTTGTGTTCATAATATTCAAC | 4 | G |
| CU-0000697 | 21060207 | TGGATCATCGTCTTTGGTTGTTGCTGGAGGTGGTC[A/G]FATTGGTGTGATGGTTGCATTGTTAGGGATGTTTG | 5 | A |
| CU-0000649 | 21068285 | TTGTTCATAGTCTTTACAACACATTAGAAGAAGAA[A/G]ITAAGGCAAGCTTCTAAGAAAGACAAAAGGAAGCT | 6 | G |
| CU-0002031 | 21144782 | TCTATAATTCCATACACACCAGGTGATGCTAAACC[A/G]GTTGCCGCGCTCATTAATAGGTTTCTAGGCTTTCC | 7 | A |

TABLE 3-continued

SNPs present in the QTL on chromosome 1. The polymorphism is indicated within brackets. The allele representative of the presence of the QTL is underlined in the bracket and reported in the last column (Tolerance T allele). The position is with respect to the cucumber genome as published: genome v2.0, Chinese Long IL 9930, available at cucurbitgenomics.org/organism/2 (based on Huang et al, 2009 and Li et al, 2011).

| SNP_id | Position | SEQ (TOP) | SEQ ID | T allele |
|---|---|---|---|---|
| CU-0000366 | 22019793 | CTAAATGTGTAACATGTTGAAACCTAGGACAAACT[A/G]GGCTTGTAGGTAGACACGGAATTAGGTTTTTTCTT | 8 | A |
| Cu-0000554 | 22180220 | ATTCCCAGCATCATACACGTAGAACTGACTCGCTA[A/C]ATAAGAACACATTCTCAAGATGTGCTTTCAATAGG | 9 | A |
| Cu-0000744 | 22190343 | CTACCATTTATAGAGTTTATAGTCGTAGAATGAAT[A/G]TGATCCATTGTCGCACCTTCAAATTGAATGCTCTT | 10 | A |
| Cu-0006168 | 22663842 | GTAGCTGTGGAGAAGGAGCAATGGTCAAGGAAAGT[A/G]AAGGCGATGGGAACCTGAGACGGTGGTGAATGCGA | 11 | G |
| Cu-0001983 | 23366713 | TCATTATAAGCTATGTTCGACTCGCAGGAGGCTTC[A/G]CATGCATACACAACAATTGTGGCCCAATCGAGCGA | 12 | G |

TABLE 4

SNPs present in the QTL on chromosome 2. The polymorphism is indicated within brackets. The allele representative of the presence of the QTL is underlined in the bracket and reported in the last column (tolerance T allele). The position is with respect to the cucumber genome as published: genome v2.0, Chinese Long IL 9930, available at cucurbitgenomics.org/organism/2 (based on Huang et al, 2009 and Li et al, 2011).

| SNP_id | Position | SEQ (TOP) | SEQ ID | T allele |
|---|---|---|---|---|
| CU-0000463 | 15987817 | GGAACAAAATATGTGGGGCAAAAGTAATTCCAAG[A/G]CAAAAACAGCCAATACACCCAAACCAAAAATTATC | 13 | A |
| CU-0001997 | 16084617 | GTGAGGGTATAGATCTTTCTGAGGCATAGAACAAC[A/G]TTTTTCTGGCAGTACATATTGCTTGTTAATGAAAT | 14 | A |
| CU-0001204 | 16163059 | TTGATTTATTTATTTCTTTTTGAAGTTGTGTTAGA[A/G]GGAAAAGGTAAGAGGGTAGGGATAATGGTTTTCAG | 15 | A |
| Cu-0003652 | 16214529 | TGTGTATTGAGTAGCGAATAAGGGAAGGAGGATTT[A/G]GGGGAAGAGAGAAAGGTGAGAGAATAAGGGAAGAA | 16 | A |
| Cu-0002682 | 16222398 | GAAAAGCCAGTTGGACGGCGGGGTGGAGGTTGGTC[A/G]TCGTACTTGCGCTTGTTGGAAGGAGTATCAGTAGC | 17 | A |
| Cu-0005012 | 16456658 | CTCTTCTTCAATGCTAAATACTTCTGGGAAAACCA[A/G]GTGTGAATCAACTGGTGAAGGGTCCGATTCGGTGT | 18 | A |
| Cu-0001371 | 16463342 | CTTACAGTGCTGCTGTTAAACTTCGGACTTGTGAG[A/G]TATAAGATTAACGCGTGAACGCTTGGGTCAAACTC | 19 | A |
| Cu-0002276 | 16649407 | TCTGTTACATGATTTGTACATGGCCAGAAGAGGAG[A/G]GTCTTTGATAGCTGTGAGAGAAAAATACAAGCTAC | 20 | A |
| Cu-0001479 | 16903104 | AAAACTTCTAAACATGAGAGTATAATATTTAAAGT[A/C]GTGCATGTAAACTGAAAGTGTTAATGACATTATGA | 21 | C |
| Cu-0006476 | 16917180 | TCTAGATCGACTGCACCATCTCCATCTTTGTCAGC[A/G]AAGCAACACCATAGTGAGCTTTCTGAAACGACATC | 22 | A |
| Cu-0003181 | 17000884 | TAAGGTTACACACAAATACACATATAGTTTTGCTT[C/G]GAAAAGCTTTTGGTCATCCTTAGGAAGTTCCTAAA | 23 | G |
| Cu-0001663 | 17004020 | GCTTGTCTAATAACAAACTGATCAACAATTTTAAC[A/G]GTGTGCACCGGATCTTGATGTGGTGCAGCCGCCTT | 24 | A |
| Cu-0001531 | 17050659 | TTCACAAACATGGTGGCTTATTATCTGATTCAGGG[A/C]GTGCTCTTGGGCGATTTCATTTTGATAAGATGAGA | 25 | A |

TABLE 4-continued

SNPs present in the QTL on chromosome 2. The polymorphism is indicated within brackets.
The allele representative of the presence of the QTL is underlined in the bracket and
reported in the last column (tolerance T allele). The position is with respect to the
cucumber genome as published: genome v2.0, Chinese Long IL 9930, available at
cucurbitgenomics.org/organism/2 (based on Huang et al, 2009 and Li et al, 2011).

| SNP_id | Position | SEQ (TOP) | SEQ ID | T allele |
|---|---|---|---|---|
| Cu-0001495 | 17203182 | CAAAATCTTGAACAATCGAAAGCTTCTTCATCAAC[A/C]TCTTCGCACGCAACTTCTTCATCTTCTCTTCTTCT | 26 | C |
| Cu-0006479 | 17291444 | ATCCCGAAACCAAAACGATGCGTAGAACAAAAGCA[G/A]CGCTAGAAGGATCGAGCCACCCGTATCAATGCATG | 27 | G |

TABLE 5

Results of the QTL analysis on the F2 population and the BC1F3. The T allele is the allele representative of the presence of the tolerance QTL and S allele is the allele representative of susceptible sequences.

| SNP_id | Chromosome | F2{-Log$_{10}$(Prob > F)} | F2(R$^2$) | BC1F3{-Log$_{10}$(Prob > F)} | BC1F3(R$^2$) | T allele | S allele |
|---|---|---|---|---|---|---|---|
| CU-0002005 | 1 | 1.56 | 0.15 | 6.56 | 0.38 | A | G |
| CU-0000824 | 1 | 1.56 | 0.15 | 6.56 | 0.38 | G | A |
| CU-0001679 | 1 | 0.12 | 0.01 | | | A | C |
| CU-0000195 | 1 | 1.62 | 0.15 | 6.95 | 0.40 | G | A |
| CU-0000697 | 1 | 1.67 | 0.09 | | | A | G |
| CU-0000649 | 1 | 1.67 | 0.09 | 7.39 | 0.42 | G | A |
| CU-0002031 | 1 | 1.12 | 0.13 | | | A | G |
| CU-0000366 | 1 | 1.54 | 0.08 | | | A | G |
| CU-0000554 | 1 | 1.18 | 0.12 | | | A | G |
| CU-0000744 | 1 | 1.67 | 0.12 | 7.94 | 0.44 | A | G |
| CU-0006168 | 1 | 3.02 | 0.12 | 6.27 | 0.37 | G | A |
| CU-0001983 | 1 | 2.26 | 0.11 | 5.67 | 0.34 | G | A |
| CU-0000463 | 2 | 1.44 | 0.06 | | | A | G |
| CU-0001997 | 2 | 0.62 | 0.06 | 6.14 | 0.36 | A | G |
| CU-0001204 | 2 | 0.60 | 0.07 | 6.14 | 0.36 | A | G |
| CU-0003652 | 2 | 0.67 | 0.07 | 6.14 | 0.36 | A | G |
| CU-0002682 | 2 | 0.67 | 0.07 | 6.14 | 0.36 | A | G |
| CU-0005012 | 2 | 2.12 | 0.07 | 6.00 | 0.35 | A | G |
| CU-0001371 | 2 | 1.96 | 0.07 | 6.00 | 0.35 | A | G |
| CU-0002276 | 2 | 2.76 | 0.08 | 6.00 | 0.35 | A | G |
| CU-0001479 | 2 | 1.79 | 0.08 | 5.37 | 0.32 | C | A |
| CU-0006476 | 2 | 2.67 | 0.05 | | | A | G |
| CU-0003181 | 2 | 2.28 | 0.05 | | | G | C |
| CU-0001663 | 2 | 2.28 | 0.05 | | | A | G |
| CU-0001531 | 2 | 1.23 | 0.08 | 4.93 | 0.30 | A | C |
| CU-0001495 | 2 | 1.64 | 0.07 | | | C | A |
| CU-0006479 | 2 | 1.65 | 0.07 | | | G | A |

REFERENCES

Huang et al. 2009. The genome of the cucumber, *Cucumis sativus* L. Nat Genet. 2009 December; 41 (12): 1275-81.

Chang et al, 2010. Identification and characterization of a mechanical transmissible begomovirus causing leaf curl on oriental melon. European Journal of Plant Pathology 127 (2): 219-228.

Tiwari et al, 2012. Molecular detection and identification of Tomato leaf curlNew Delhi virus isolate causing yellow mosaic disease in Bitter gourd (*Momordica charantia*), a medicinallyimportant plant in India. Medicinal Plants, 2 (2). 117-123.

Gao et al. 2016. DNA-guided genome editing using the Natronobacterium gregoryi Argonaute. Nature Biotechnology volume 34, pages 768-773.

Islam, S. et al. 2011. Screening of *Luffa cylindrica* Roem against tomato leaf curl New Delhi virus, inheritance of resistance and identification of SRAP markers linked to resistance gene. Journal of Horticulture Science and Biotechnology 86 (6): 661-667.

Kirkbride, J. H., Jr. 1993. Biosystematic monograph of the genus *Cucumis* (Cucurbitaceae). 84.

Li, Z. et al. 2011. RNA-Seq improves annotation of protein-coding genes in the cucumber genome. BMC Genomics 12:540.

Lopez, C. et al. 2015. Mechanical transmission of Tomato leaf curl New Delhi virus to cucurbit germplasm: selection of tolerance sources in *Cucumis melo*. Eupphytica 204:679-691.

Ranjan et al 2015. Evaluation of cucumber (*Cucumis sativus*) germplasm for agronomic traits and disease resistance and estimation of genetic variability. Indian Journal of Agricultural Sciences 85 (2): 234-9.

Ruiz et al 2015. First Report of Tomato leaf curl New Delhi virus Infecting Tomato in Spain. The American Phytopathological Society. Vol. 99, No. 6, p. 894.

Saeed M. et al. 2007. A monopartite begomovirus-associated DNA beta satellite substitutes for the DNA B of a bipartite begomovirus to permit systemic infection. J Gen Virol. 88 (Pt 10): 2881-9.

The invention claimed is:

1. A *Cucumis sativus* var. *sativus* plant tolerant to Tomato leaf curl New Delhi virus (ToLCNDV), comprising in its genome the combination of a first quantitative trait locus (QTL) QTL1 on chromosome 1 and a second QTL, QTL2 on chromosome 2, at least one of QTL1 and QTL2 being homozygous, wherein said combination confers to the plant tolerance to ToLCNDV, wherein said QTL1 is located on chromosome 1, within the chromosomal region delimited by allele A of CU-0002005, the sequence of which is set forth in SEQ ID NO: 1, and allele G of CU-0001983, the sequence of which is set forth in SEQ ID NO: 12, and said QTL2 is located on chromosome 2, within the chromosomal region delimited by allele A of CU-0000463, the sequence of which is set forth in SEQ ID NO: 13, and allele G of CU-0006479, the sequence of which is set forth in SEQ ID NO:27, wherein said plant is a commercial gynoecious cucumber or a monoecious cucumber, with at least 50% of gynoecious flowers, and wherein said QTLs on chromosomes 1 and 2 are the same as those present in the genome of the seeds of plant designated TOCUR6080, deposited with NCIMB under accession number 43427.

2. The plant according to claim 1, wherein said plant has less than 3 primary branches.

3. The plant according to claim 1, wherein said plant is a progeny of the plant designated TOCUR6080, seeds thereof have been deposited at the NCIMB, under NCIMB accession number 43427.

4. The plant according to claim 1, comprising a further QTL on chromosome 4 imparting tolerance to ToLCNDV, wherein said QTL is characterized by allele A of SNP markers CU-0000290, the sequence of which is set forth in SEQ ID NO: 28.

5. The plant according to claim 1 also containing in its genome sequences conferring resistance to Powdery Mildew, or to potyviruses.

6. A cell of the *Cucumis sativus* var. *sativus* plant according to claim 1, comprising in its genome said QTL1 on chromosome 1, and said QTL2 on chromosome 2, conferring tolerance to ToLCNDV in cucumber when combined, wherein at least one of the QTL is present homozygously.

7. The cell according to claim 6, wherein said cell is a regenerable cell, or a non regenerable cell.

8. A plant part of the *Cucumis sativus* var. *sativus* plant according to claim 1, wherein said plant part comprises cells comprising in their genome said QTL1 on chromosome 1, and said QTL2 on chromosome 2, conferring tolerance to ToLCNDV in cucumber when combined, wherein at least one of the QTL is present homozygously.

9. Seed of a *Cucumis sativus* var. *sativus* plant, which develops into the plant according to claim 1.

10. A tissue culture of cells of the plant according to claim 1, wherein the cells are derived from embryos, protoplasts, meristematic cells, callus, pollen, leaves, anthers, stems, petioles, roots, root tips, seeds, flowers, cotyledons, and/or hypocotyls, and contain in their genome said QTL1 on chromosome 1 and said QTL2 on chromosome 2 conferring tolerance to ToLCNDV, wherein at least one of said QTLs is present homozygously.

11. A method for breeding *Cucumis sativus* plants having resistance to ToLCNDV, comprising the step of crossing a plant grown from the deposited seeds NCIMB 43427 or progeny thereof comprising QTL1 and QTL2 conferring when combined ToLCNDV tolerance, with an initial *Cucumis sativus* plant devoid of said QTLs, wherein said QTL1 on chromosome 1 and QTL2 on chromosome 2 are the same as those present in the genome of the seeds of plant designated TOCUR6080, which have been deposited with NCIMB under accession number 43427; and wherein said QTL1 is located on chromosome 1, within the chromosomal region delimited by allele A of CU-0002005 and allele G of CU-0001983, and wherein said QTL2 is located on chromosome 2, within the chromosomal region delimited by allele A of CU-0000463 and allele G of CU-0006479.

12. The method according to claim 11, further comprising the steps of:
a) Selecting a plant in the progeny obtained from said step of crossing, said selected plant comprising QTL1 and QTL2; and
b) Optionally self-pollinating one time or more times the plant selected at step a) and selecting in the progeny thus obtained a plant having tolerance to ToLCNDV, wherein said QTLs on chromosomes 1 and 2 are the same as those present in the genome of the seeds of plant designated TOCUR6080, which have been deposited with NCIMB under accession number 43427.

13. The method according to claim 11, further comprising the steps of:
a) Selfing F1 hybrids obtained from said step of crossing, to create an F2 population, and
b) Selecting individuals in the progeny thus obtained having tolerance to ToLCNDV,
wherein said QTLs on chromosomes 1 and 2 are the same as those present in the genome of the seeds of plant designated TOCUR6080, which have been deposited with NCIMB under accession number 43427.

14. A *Cucumis sativus* plant obtained by the method according to claim 11, comprising said QTL1 on chromosome 1 and said QTL2 on chromosome 2, at least one of QTL1 and QTL2 being homozygous.

15. A method for reducing the loss on cucumber production in condition of ToLCNDV infestation, comprising growing the cucumber plant according to claim 1.

16. A method for selecting cucumber plants having two QTLs, conferring tolerance to ToLCNDV when combined, said method comprising:
a) Assaying cucumber plants for the presence of at least two genetic markers, genetically linked to 2 QTLs conferring when combined tolerance to ToLCNDV in cucumber,
b) Selecting a plant comprising the genetic markers and the QTLs conferring tolerance to ToLCNDV,
wherein the QTLs and the genetic markers are to be found in the chromosomal region delimited on chromosome 1 by allele A of CU-0002005, the sequence of which is set forth in SEQ ID NO: 1, and allele G of CU-0001983, the sequence of which is set forth in SEQ ID NO: 12, and in the chromosomal region delimited on chromosome 2 by allele A of CU-0000463, the sequence of which is set forth in SEQ ID NO: 13, and allele G of CU-0006479, the sequence of which is set forth in SEQ ID NO: 27, and
wherein said QTLs on chromosomes 1 and 2 are the same as those found in the genome of the seeds of plant designated TOCUR6080, deposited with NCIMB under accession number 43427.

17. The method according to claim 16, said method further comprising detection of the following alleles: allele A of CU-0002031, the sequence of which is set forth in SEQ ID NO:7, allele A of CU-0000366, the sequence of which is set forth in SEQ ID NO:8 or allele A of CU-0000744, the sequence of which is set forth in SEQ ID NO:10 on chromosome 1, in combination with allele A of CU-0002682, the sequence of which is set forth in SEQ ID NO:17, or allele A of CU-0005012 the sequence of which is set forth in SEQ ID NO:18 on chromosome 2, in the genetic material sample of the selected plant.

\* \* \* \* \*

SEQUENCE LISTING

<160> NUMBER OF SEQ ID NOS: 28

<210> SEQ ID NO 1
<211> LENGTH: 71
<212> TYPE: DNA
<213> ORGANISM: Cucumis sativus
<220> FEATURE:
<221> NAME/KEY: polymorphism
<222> LOCATION: (36)..(36)
<223> OTHER INFORMATION: susceptible = G; tolerant = A

<400> SEQUENCE: 1
catgtctgtc caaacaacaa aacagagaag ctcacraagt atagataatt aaacaaagtt    60
tgttctctaa g                                                         71

<210> SEQ ID NO 2
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = G

<400> SEQUENCE: 2
ttactttttg gcttcaaatt ggtttggggt tgagarcttt gaatttctgt ggcagtgggg    60
tgttagtgtg t                                                         71

<210> SEQ ID NO 3
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = C; tolerant = A

<400> SEQUENCE: 3
ctgatgaagc ataaagaatg agttacactt cagcgmttat tacactaaga aaatagttaa    60
acttcaagtc c                                                         71

<210> SEQ ID NO 4
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = G

<400> SEQUENCE: 4
tagttatcaa ttggaaggaa cttggcgtat cgctcrgcct tcgctcctga tttgtgttca    60
taatattcaa c                                                         71

<210> SEQ ID NO 5
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 5
tggatcatcg tctttggttg ttgctggagg tggtcrtatt ggtgtgatgg ttgcattgtt    60 aggqatgttt g                                                                71

<210> SEQ ID NO 6
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = G

<400> SEQUENCE: 6
ttgttcatag tctttacaac acattagaag aagaarttaa ggcaagcttc taagaaagac    60
aaaaggaagc t                                                          71

<210> SEQ ID NO 7
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 7
tctataattc catacacacc aggtgatgct aaaccrgttg ccgcgctcat taataggttt    60
ctaggctttc c                                                          71

<210> SEQ ID NO 8
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 8
ctaaatgtgt aacatgttga aacctaggac aaactrggct tgtaggtaga cacggaatta    60
ggttttttct t                                                          71

<210> SEQ ID NO 9
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = C; tolerant = A

<400> SEQUENCE: 9
attcccagca tcatacacgt agaactgact cgctamataa gaacacattc tcaagatgtg    60
ctttcaatag g                                                          71

<210> SEQ ID NO 10
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 10
ctaccattta tagagtttat agtcgtagaa tgaatrtgat ccattgtcgc accttcaaat    60
tgaatgctct t                                                         71

<210> SEQ ID NO 11
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = G

<400> SEQUENCE: 11
gtagctgtgg agaaggagca atggtcaagg aaagtraagg cgatgggaac ctgagacggt    60
ggtgaatgcg a                                                         71

<210> SEQ ID NO 12
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = G

<400> SEQUENCE: 12
tcattataag ctatgttcga ctcgcaggag gcttcrcatg catacacaac aattgtggcc    60
caatcgagcg a                                                         71

<210> SEQ ID NO 13
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 13
ggaacaaaat atgtgggggc aaaagtaatt ccaagrcaaa aacagccaat acacccaaac    60
caaaaattat c                                                         71

<210> SEQ ID NO 14
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 14
gtgagggtat agatctttct gaggcataga acaacrtttt tctggcagta catattgctt    60
gttaatgaaa t                                                         71

<210> SEQ ID NO 15
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 15

```
ttgatttatt tatttctttt tgaagttgtg ttagarggaa aaggtaagag ggtagggata    60
atggttttca g                                                        71
```

<210> SEQ ID NO 16
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 16

```
tgtgtattga gtagcgaata agggaaggag gatttrgggg aagagagaaa ggtgagagaa    60
taagggaaga a                                                        71
```

<210> SEQ ID NO 17
<211> LENGTH: 71
<212> TYPE: DNA
<213> ORGANISM: Cucumis sativus
<220> FEATURE:
<221> NAME/KEY: polymorphism
<222> LOCATION: (36)..(36)
<223> OTHER INFORMATION: susceptible = G; tolerant = A

<400> SEQUENCE: 17

```
gaaaagccag ttggacggcg gggtggaggt tggtcrtcgt acttgcgctt gttggaagga    60
gtatcagtag c                                                        71
```

<210> SEQ ID NO 18
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 18

```
ctcttcttca atgctaaata cttctgggaa aaccargtgt gaatcaactg gtgaagggtc    60
cgattcggtg t                                                        71
```

<210> SEQ ID NO 19
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 19

```
cttacagtgc tgctgttaaa cttcggactt gtgagrtata agattaacgc gtgaacgctt    60
gggtcaaact c                                                        71
```

<210> SEQ ID NO 20
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 20
tctgttacat gatttgtaca tggccagaag aggagrgtct ttgatagctg tgagagaaaa    60
atacaagcta c                                                         71

<210> SEQ ID NO 21
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = C

<400> SEQUENCE: 21
aaaacttcta aacatgagag tataatattt aaagtmgtgc atgtaaactg aaagtgttaa    60
tgacattatg a                                                         71

<210> SEQ ID NO 22
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 22
tctagatcga ctgcaccatc tccatctttg tcagcraagc aacaccatag tgagctttct    60
gaaacgacat c                                                         71

<210> SEQ ID NO 23
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = C; tolerant = G

<400> SEQUENCE: 23
taaggttaca cacaaataca catatagttt tgcttsgaaa agcttttggt catccttagg    60
aagttcctaa a                                                         71

<210> SEQ ID NO 24
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = G; tolerant = A

<400> SEQUENCE: 24
gcttgtctaa taacaaactg atcaacaatt ttaacrgtgt gcaccggatc ttgatgtggt    60
gcagccgcct t                                                         71

<210> SEQ ID NO 25
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = C; tolerant = A

```
<400> SEQUENCE: 25
ttcacaaaca tggtggctta ttatctgatt cagggmgtgc tcttgggcga tttcattttg    60
ataagatgag a                                                        71

<210> SEQ ID NO 26
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = C

<400> SEQUENCE: 26
caaaatcttg aacaatcgaa agcttcttca tcaacmtctt cgcacgcaac ttcttcatct    60
tctcttcttc t                                                        71

<210> SEQ ID NO 27
<211> LENGTH: 71
<212> TYPE: DNA
<213> ORGANISM: Cucumis sativus
<220> FEATURE:
<221> NAME/KEY: Polymorphism
<222> LOCATION: (36)..(36)
<223> OTHER INFORMATION: susceptible = A; tolerant = G

<400> SEQUENCE: 27
atcccgaaac caaaacgatg cgtagaacaa aagcarcgct agaaggatcg agccacccgt    60
atcaatgcat g                                                        71

<210> SEQ ID NO 28
<211> LENGTH: 201
<212> TYPE: DNA
<213> ORGANISM: Cucumis sativus
<220> FEATURE:
<221> NAME/KEY: Polymorphism
<222> LOCATION: (101)..(101)
<223> OTHER INFORMATION: susceptible = G; tolerant = A

<400> SEQUENCE: 28
ttgggaatgc aaaacacatc atcgataaca tgtaagtttg aaagtatgaa atgtaacctt    60 cccctacag attgctgctt agctccatgc atatagagtc rtcagtaaac tatattatac   120
actctttaag agttgctgct tctaggcaaa ccttttgatt gtctctatac ccayctcttt   180
tgtcaacaag ggaacactta t                                            201
```